US011895256B2

(12) United States Patent
Hatch et al.

(10) Patent No.: US 11,895,256 B2
(45) Date of Patent: Feb. 6, 2024

(54) HALL MONITOR FOR A HEALTH CARE FACILITY

(71) Applicant: Hatchmed Corporation, Seattle, WA (US)

(72) Inventors: Brian Hatch, Seattle, WA (US); Kyrylo Keydanskyy, Seattle, WA (US)

(73) Assignee: Hatchmed Corporation, Seattle, WA (US)

( * ) Notice: Subject to any disclaimer, the term of this patent is extended or adjusted under 35 U.S.C. 154(b) by 500 days.

(21) Appl. No.: 17/087,392

(22) Filed: Nov. 2, 2020

(65) Prior Publication Data

US 2021/0051223 A1    Feb. 18, 2021

Related U.S. Application Data

(63) Continuation-in-part of application No. 16/827,554, filed on Mar. 23, 2020, now Pat. No. 10,863,012, (Continued)

(51) Int. Cl.
*H01R 13/46*    (2006.01)
*H01R 13/62*    (2006.01)
(Continued)

(52) U.S. Cl.
CPC ............. *H04M 1/04* (2013.01); *A61B 5/7445* (2013.01); *G06F 1/1632* (2013.01); (Continued)

(58) Field of Classification Search
CPC .. H04M 1/04; H04M 1/72541; H04M 1/7224; A61B 5/7445; A61B 5/74; (Continued)

(56) References Cited

U.S. PATENT DOCUMENTS 3,316,044 A    4/1967  Carbary
3,942,751 A    3/1976  Fay
(Continued)

FOREIGN PATENT DOCUMENTS

CN    201479176    5/2010
CN    202949471    5/2013
(Continued)

OTHER PUBLICATIONS

U.S. Appl. No. 17/402,397, "Notice of Allowance", dated Mar. 27, 2023, 15 pages.
(Continued)

*Primary Examiner* — Angel R Estrada
(74) *Attorney, Agent, or Firm* — Kilpatrick Townsend & Stockton LLP

(57) ABSTRACT

A system comprising a housing, the housing comprising an opening through which a display of an electronic device is accessible by a user, peripheral device(s) connected to the housing and controllable by the electronic device, and a hub contained within the housing. The hub comprises a first interface to couple the hub with the electronic device, a second interface for coupling the peripheral device(s), a processor, and a non-transitory memory having instructions stored thereon that, when executed by the processor cause the processor to perform operations. The operations comprising receiving first input data from the electronic device and sending first output data from the hub to the one or more peripheral devices based on the first input data. The operations further comprising receiving second input data from the peripheral device(s) and sending second output data from the hub to the electronic device based on the second input data.

10 Claims, 23 Drawing Sheets

Related U.S. Application Data which is a continuation of application No. 16/035,283, filed on Jul. 13, 2018, now Pat. No. 10,601,971.

(60) Provisional application No. 63/065,349, filed on Aug. 13, 2020, provisional application No. 62/567,670, filed on Oct. 3, 2017.

(51) Int. Cl.

| *H04M 1/04* | (2006.01) |
|---|---|
| *A61B 5/00* | (2006.01) |
| *G08B 25/01* | (2006.01) |
| *G06F 1/16* | (2006.01) |
| *G08B 25/08* | (2006.01) |
| *A61G 7/05* | (2006.01) |
| *H04M 1/72424* | (2021.01) |

(52) U.S. Cl.
CPC ........... *G08B 25/016* (2013.01); *G08B 25/08* (2013.01); *A61G 7/0524* (2016.11); *A61G 2203/20* (2013.01); *H01R 13/6205* (2013.01); *H01R 2201/12* (2013.01); *H04M 1/72424* (2021.01)

(58) Field of Classification Search
CPC ... G06F 1/1632; G06F 1/1633; G08B 25/016; G08B 25/08; A61G 7/0524; A61G 2203/20; H01R 13/6205; H01R 2201/12; H01R 13/46; H02G 3/08; H02G 3/081
USPC ... 174/50, 480, 482, 500, 501, 503, 520, 58, 174/61; 220/3.2, 3.3, 4.02; 248/906, 248/200; 5/503.1, 658
See application file for complete search history.

(56) References Cited

U.S. PATENT DOCUMENTS

| 4,680,790 | A | 7/1987 | Packard et al. |
|---|---|---|---|
| 5,273,354 | A | 12/1993 | Herrmann et al. |
| 5,701,991 | A | 12/1997 | Helmetsie |
| 5,802,636 | A | 9/1998 | Corbin et al. |
| 5,867,821 | A | 2/1999 | Ballantyne et al. |
| 6,206,464 | B1 | 3/2001 | Santa Rosa et al. |
| 6,339,410 | B1 | 1/2002 | Milner et al. |
| 6,407,335 | B1 | 6/2002 | Franklin-lees et al. |
| 6,486,792 | B1 | 11/2002 | Moster et al. |
| 6,622,980 | B2 | 9/2003 | Boucher et al. |
| 7,301,451 | B2 | 11/2007 | Hastings |
| 7,349,203 | B2 | 3/2008 | Jobs et al. |
| 7,458,555 | B2 | 12/2008 | Mastropaolo et al. |
| 7,730,565 | B1 | 6/2010 | Masson |
| 7,778,848 | B1 | 8/2010 | Reeves |
| 7,821,782 | B2 | 10/2010 | Doherty et al. |
| 7,861,985 | B2 | 1/2011 | Galvin |
| 7,967,137 | B2 | 6/2011 | Fulbrook et al. |
| 7,971,289 | B2 | 7/2011 | Payne et al. |
| 8,011,629 | B2 | 9/2011 | Herskovic |
| 8,020,829 | B1 | 9/2011 | Tamayori |
| 8,053,670 | B2 | 11/2011 | Lin et al. |
| 8,461,968 | B2 | 6/2013 | Ball et al. |
| 8,485,404 | B2 | 7/2013 | Monaco et al. |
| 8,499,384 | B2 | 8/2013 | Zerhusen |
| D692,439 | S | 10/2013 | Muhlenberg |
| 8,602,662 | B1 | 12/2013 | Mans |
| 8,607,388 | B1 | 12/2013 | Flanagan et al. |
| 8,650,682 | B2 | 2/2014 | Herman |
| 8,661,583 | B2 | 3/2014 | Chinn et al. |
| 8,727,804 | B2 | 5/2014 | McNeely et al. |
| 8,763,802 | B2 | 7/2014 | Ellis-Brown |
| 8,789,802 | B2 | 7/2014 | Springer et al. |
| 8,794,766 | B2 | 8/2014 | Listou |
| 8,867,198 | B2 | 10/2014 | Steele |
| 8,917,496 | B2 | 12/2014 | Richardson et al. |
| 8,944,826 | B1 | 2/2015 | Wilkolaski et al. |
| 8,994,776 | B2 | 3/2015 | Sutherland et al. |
| 9,038,971 | B1 | 5/2015 | Guthrie |
| 9,147,965 | B2 | 9/2015 | Lee |
| 9,243,839 | B2 | 1/2016 | Kim et al. |
| 9,286,441 | B2 | 3/2016 | Zerhusen et al. |
| 9,375,374 | B2 | 6/2016 | Herman et al. |
| 9,444,237 | B2 | 9/2016 | Frojo |
| 9,463,126 | B2 | 10/2016 | Zerhusen et al. |
| D773,465 | S | 12/2016 | Palmer et al. |
| 9,573,686 | B2 | 2/2017 | Barth |
| 9,643,767 | B2 | 5/2017 | Ziemba |
| 9,680,518 | B2 | 6/2017 | Wojcik et al. |
| 9,743,357 | B2 | 8/2017 | Tabe |
| 9,824,815 | B2 | 11/2017 | Leabman et al. |
| 10,013,868 | B2 | 7/2018 | Cox et al. |
| 10,028,875 | B2 | 7/2018 | Hatch |
| 10,175,723 | B2 | 1/2019 | Weldon |
| 10,601,971 | B2 | 3/2020 | Hatch et al. |
| 10,863,012 | B2 | 12/2020 | Hatch et al. |
| 11,727,768 | B2 | 8/2023 | Hatch et al. |
| 2001/0022719 | A1 | 9/2001 | Armitage et al. |
| 2004/0174107 | A1 | 9/2004 | O'Halloran |
| 2005/0062380 | A1 | 3/2005 | Park et al. |
| 2009/0212925 | A1 | 8/2009 | Schuman et al. |
| 2009/0255292 | A1 | 10/2009 | Benz |
| 2010/0064721 | A1 | 3/2010 | Shin et al. |
| 2010/0132122 | A1 | 6/2010 | Hollingshead |
| 2011/0210833 | A1 | 9/2011 | McNeely et al. |
| 2011/0214234 | A1 | 9/2011 | Herman |
| 2011/0290807 | A1 | 12/2011 | Calvillo et al. |
| 2012/0026684 | A1 | 2/2012 | Matthews |
| 2012/0215360 | A1 | 8/2012 | Zerhusen et al. |
| 2012/0323090 | A1 | 12/2012 | Bechtel et al. |
| 2013/0093388 | A1 | 4/2013 | Partovi |
| 2013/0314866 | A1 | 11/2013 | Millman |
| 2015/0024611 | A1 | 1/2015 | Wilkolaski et al. |
| 2015/0351530 | A1 | 12/2015 | Udagawa et al. |
| 2016/0008197 | A1 | 1/2016 | Zerhusen et al. |
| 2016/0047594 | A1 | 2/2016 | Choo et al. |
| 2016/0128468 | A1 | 5/2016 | Lafleche et al. |
| 2016/0183393 | A1 | 6/2016 | Groom et al. |
| 2016/0190838 | A1 | 6/2016 | Webb |
| 2016/0228091 | A1 | 8/2016 | Chiang et al. |
| 2016/0324701 | A1 | 11/2016 | Cambridge et al. |
| 2017/0035295 | A1 | 2/2017 | Collins, Jr. et al. |
| 2017/0052581 | A1 | 2/2017 | Enzinna |
| 2017/0223482 | A1 | 8/2017 | Park et al. |
| 2018/0168900 | A1 | 6/2018 | McNeely et al. |
| 2020/0381094 | A1 | 12/2020 | Myers et al. |
| 2021/0051222 | A1 | 2/2021 | Hatch et al. |
| 2022/0051532 | A1 | 2/2022 | Hatch et al. |

FOREIGN PATENT DOCUMENTS

| EP | 2575263 | 4/2013 |
|---|---|---|
| KR | 20130004443 | 7/2013 |
| KR | 20170035851 | 3/2017 |
| WO | 2016155691 | 12/2016 |
| WO | 2016196403 | 12/2016 |
| WO | 2017131796 | 8/2017 |

OTHER PUBLICATIONS

"2014 Manufacturers' Excellence Awards Finalists", Crestron Pyng™, Available Online at: http://cedia.net/programs/awards/winners/2014-manufacturers%27-excellence-awards-fina . . . , Accessed from Internet on Jul. 29, 2019, 15 pages.

"Announcing New Savant Home Automation Partners: Nest and iPort", Inc, Available Online at: https://inctech.net/savant-announces-new-home-automation-partners/, Sep. 27, 2016, 2 pages.

"Camera SnakeClamp", Snake Clamp, Available on Internet at: https://web.archive.org/web/20121220014228/https://snakeclamp.com/Category/camera-snakeclamp-withflexible-gooseneck-arm#. WeENSuT2Z9A, Dec. 12, 2012, 3 pages.

Google Search, "iport OR OR OR Dana Innovations Surface Mount with Buttons• OR Launch Port with Buttons•", Available Online at:

(56) References Cited

OTHER PUBLICATIONS https://www.google.com/search?q=iport+OR+OR+OR+"dana+innovations"+"surface+mount+with+buttons•+OR+"launch+port+with+buttons•&rlz . . . , Accessed from Internet on Jul. 29, 2019, 2 pages.

"iPort® Announces the xPRESS™ Audio Keypad for Sonos®: Direct WiFi Control for Any Sonos Device", Available Online at: https://www.prnewswire.com/news-releases/iport-announces-the-xpress-audio-keypad-for-sonos-direct-wifi-control-for-any-sonos-device-300320239.h . . . , Aug. 30, 2016, 3 pages.

"Medical-Grade Tablet Cases Beat Pathogens", Maximise Technology, Available online at: https://www.maximisetechnology.com.au/medical-grade-device-cases-beat-pathogens-for-health-care/, 2019, 4 pages.

"Quality Gaming and Multimedia Accessories", CTA®, [online] ctadigital.com, Available Online at: http://web.archive.org/web/20160424204832/http://www.ctadigital.com:80/, Apr. 24, 2016, 5 pages.

"RAM® Torque ¾™—1" Diameter Handlebar/Rail are with 1", Ball Medium Arm and X-Grip® Mounts,, Available Online at: https://web.archive.org/web/20160616011725/http:www.rammount.com/part RAM-B-408-75-1-UN7U, Jun. 6, 2016, 9 pages.

"REGO Patient Interaction System", Curbell Medical, Online Available at: https://hellorego.com/, 8 pages.

"Roomie Remote Launches 3.0 App for Home Theater and Home Automation at a Fraction of the Cost of Traditional Touch Panei Systems", Available Online at: https://dialog.proquest.com/professional/printviewfile?accountid=157769, Sep. 30, 2014, 2 pages.

"Savant Home Automation Works with Nest and iPort, Integrates Deeper with Sonos, PureLink", Available Online at: https://www.cepro.com/article/savant_home_automation_works_with_nest_iport_integrates_deeper_with_sonos, Sep. 27, 2016, 2 pages.

"SVI Trade Awards 2017—The Winners!", Available Online at: https://wws.v.svimag.com/news/svi_trade_awards_2017_the_winners, Apr. 27, 2017, 5 pages.

U.S. Appl. No. 15/705,105, "Non Final Office Action", dated Nov. 14, 2017, 6 pages.

U.S. Appl. No. 15/705,105, "Notice of Allowance", dated Mar. 27, 2018, 5 pages.

U.S. Appl. No. 16/035,283, "Notice of Allowance", dated Jan. 17, 2020, 9 pages.

U.S. Appl. No. 16/827,554, "Non-Final Office Action", dated Jun. 12, 2020, 7 pages.

U.S. Appl. No. 16/827,554, "Notice of Allowance", dated Aug. 5, 2020, 8 pages.

HALL MONITOR FOR A HEALTH CARE FACILITY

CROSS-REFERENCES TO RELATED APPLICATIONS

This application is a continuation-in-part of U.S. patent application Ser. No. 16/827,554, filed Mar. 23, 2020 which application is a continuation of U.S. patent application Ser. No. 16/035,283, filed Jul. 13, 2018, and now granted as U.S. Pat. No. 10,601,971, which application claims the benefit of U.S. Provisional Application No. 62/567,670, filed Oct. 3, 2017. This application also claims the benefit of U.S. Provisional Application No. 63/065,349, filed Aug. 13, 2020, the entire contents of all which are hereby incorporated for all purposes in their entirety.

BACKGROUND OF THE INVENTION

Portable electronic devices (PEDs) (e.g., digital tablets, smart phones, and other electronic devices) are becoming more popular and prevalent in modern day lifestyles. Hospitals are experiencing increased usage of PEDs, either by patients and/or by hospital personnel. PEDs are being used in hospitals for communication, education, video conferencing with a patient who is in a hospital bed, and entertainment of the patient.

BRIEF SUMMARY

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

Embodiments herein are directed to portable electronic device (PED) related assemblies that are employable in a health care facility and can support the use of a PED or other electronic device on a wall of the health care facility to provide access to data and receive inputs and/or signals from users. In some embodiments, a PED related assembly includes one or more communication, data, and/or power cable assemblies that can be readily disconnected interchange, remove, or otherwise interact with the device. In some embodiments, a PED related assembly includes a PED holder with an output connector that is connectable to an input port of a PED held in the PED holder. As a result, a PED can be supplied power and/or data via a connection that enables use of the PED.

One general aspect includes a surface-mounted electronic device holder including a housing to contain an electronic device including a display, the housing including a first portion adapted for mounting the surface-mounted electronic device to a surface of a health care facility, the housing also including a second portion defining an opening through which the display is accessible by a user; and one or more interfaces adapted for connection to at least one of a power or a data cable of a health care facility, the one or more interfaces disposed in the housing. The surface—mounted electronic device holder also includes a first interface of the one or more interfaces is operatively coupleable with the electronic device such that power received from the power and data cable is provided from the first interface to the electronic device. The surface—mounted electronic device holder also includes a second interface of one of the one or more interfaces is operatively coupled with a communication system of the health care facility such that a signal is provided from the second interface to the communication system via the power and data cable.

Implementations may include one or more of the following features. The surface-mounted electronic device holder further including one or more color-configurable lights positioned around a perimeter of the housing. The surface-mounted electronic device holder further including a projector to project graphical information on a wall, door, ceiling, or floor of the health care facility. The surface-mounted electronic device holder further including a proximity sensor communicatively coupled to the electronic device and configured to activate the electronic device when an individual is within a predetermined threshold distance of the surface-mounted electronic device holder. The surface-mounted electronic device holder further including an authentication sensor to detect credentials of an individual and convey the credentials to the electronic device or health care facility for authorization to display patient information on the display. The surface-mounted electronic device holder further including a physical button on the housing, enabling an individual to interact with the electronic device. The surface-mounted electronic device holder where the housing further includes internal cradling to support the electronic device aligned with the opening, the internal cradling including posts positioned to retain edges of the electronic device, where each post includes an l-shaped protrusion at a distal end of the post, the l-shaped protrusion for partially surrounding a corner of the electronic device. The surface-mounted electronic device holder where the first portion and the second portion are coupled with a locking connection including at least one of a magnetic slider, a security screw, or a hidden screw.

One general aspect includes a surface-mounted electronic device holder, the surface-mounted electronic device holder including an electronic device including a processor, memory, and visual interface. The surface—mounted electronic device holder also includes a housing enclosing a space to contain the electronic device. The surface—mounted electronic device holder also includes an interface operatively coupleable with the electronic device such that power received from a power over ethernet (POE) cable is provided from the interface to the electronic device. The surface—mounted electronic device holder also includes an authentication device to receive authentication data and provide the authentication data to the electronic device. The surface—mounted electronic device holder also includes one or more configurable light emitting devices positioned on the housing.

Implementations may include one or more of the following features. The surface-mounted electronic device holder where the one or more configurable light emitting devices are configurable, by the electronic device, based at least in part on a room status. The surface-mounted electronic device holder where the authentication device includes an RFID reader configured to receive RFID information from an RFID device of a user. The surface-mounted electronic device holder further including a camera for capturing image data of an individual outside adjacent the housing. The surface-mounted electronic device holder where the one or more configurable light emitting devices selectively illuminate based on a signal from the electronic device indicating a condition within a room adjacent the surface-mounted electronic device holder. The surface-mounted electronic device holder further including a proximity sensor communicatively coupled to the electronic device and configured to wake the electronic device when an individual is within a predetermined threshold distance of the surface-mounted electronic device holder. The surface-mounted electronic device holder further including an authentication sensor communicatively coupled to the electronic device and configured to receive authentication credentials from an individual and convey the authentication credentials to the electronic device for use in selectively displaying patient information on the display of the electronic device. The surface-mounted electronic device holder where the interface is operatively coupled to one or more devices located within a room adjacent the surface-mounted electronic device holder. The surface-mounted electronic device holder where the interface operatively couples the electronic device to a patient bed to provide patient bed status information at a display of the electronic device. The surface-mounted electronic device holder further including a physical button on the housing, enabling an individual to interact with the electronic device.

One general aspect may include a method, including placing a housing of a surface-mounted electronic device holder on a wall adjacent a patient room of a health care facility. The method also includes placing an electronic device within the housing. The method also includes connecting the electronic device to a power and data cable, the power and data cable operably coupling the electronic device to one or more systems of a health care facility. The method also includes connecting the electronic device to a light emitting device connected to the housing. The method also includes securing the electronic device within the housing.

Implementations may include one or more of the following features. The method where the housing includes a first portion and a second portion, the first portion and the second portion enclosing a space to contain an electronic device including a display and the first portion defining an opening through which the display is accessible by a user, and one or more interfaces adapted for connection to the power and data cable, the one or more interfaces disposed in the housing. The method further including connecting the electronic device to a sensor, the sensor configured to detect information relating to an individual outside the patient room and convey the information to the electronic device for selectively presenting patient information on a display of the electronic device in response to receiving the information.

A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions. One general aspect includes a method, including displaying, on a display of an electronic device in a surface-mounted electronic device holder associated with a patient room, a first set of information including data corresponding to a status of the patient room. The method also includes receiving authentication information, via an authentication sensor, associated with an individual located in proximity to the surface-mounted electronic device. The method also includes displaying, on the display, a second set of information in response to receiving the authentication information, the second set of information including data corresponding to a patient within the patient room. Other embodiments of this aspect include corresponding computer systems, apparatus, and computer programs recorded on one or more computer storage devices, each configured to perform the actions of the methods.

For a fuller understanding of the nature and advantages of the present invention, reference should be made to the ensuing detailed description and accompanying drawings.

BRIEF DESCRIPTION OF THE DRAWINGS

The specification makes reference to the following appended figures, in which use of like reference numerals in different figures is intended to illustrate like or analogous components.

DETAILED DESCRIPTION

Figure 1:
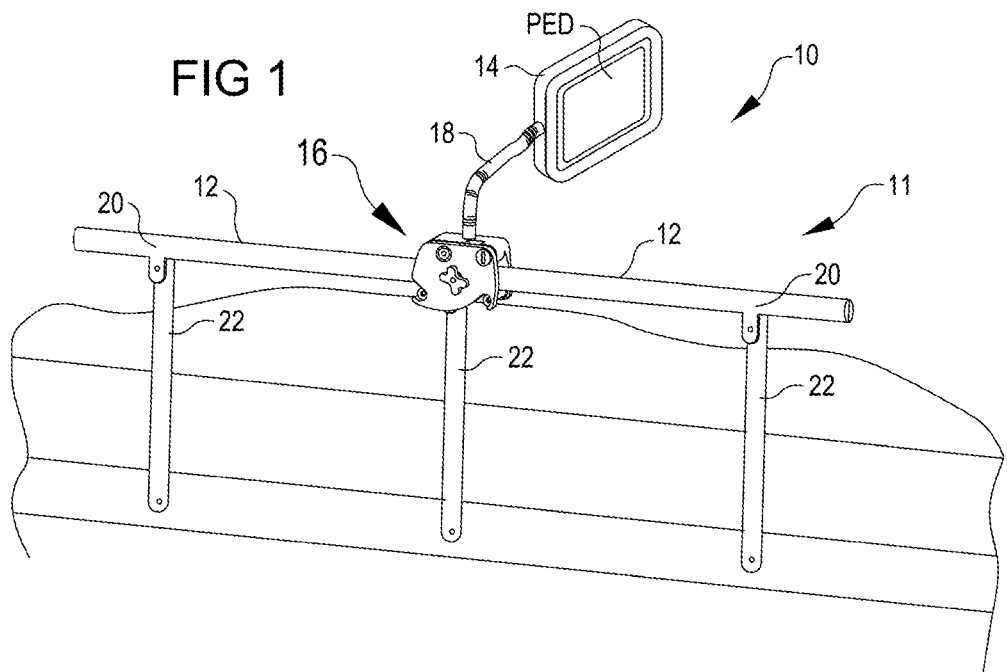
FIG. 1 shows a portable electronic device (PED) holder assembly that includes a bed connector that attaches to a side rail of the patient bed, in accordance with embodiments.

In the following description, various embodiments of the present invention are described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

As is known, a hospital bed or hospital stretcher is a patient holder assembly specially designed for hospitalized patients or others in need of some form of health care. As used herein throughout this disclosure, a "bed" refers to any patient holder assembly. Hospital beds have special features both for the comfort and well-being of the patient and for the convenience of health care workers. Common features include adjustable height for the entire bed, the head, and the feet, adjustable side rails, and electronic buttons to operate both the bed and other nearby electronic devices. Hospital beds and other similar types of beds are used not only in hospitals, but in other health care facilities and settings, such as nursing homes, assisted living facilities, outpatient clinics, and in home health care.

Many hospital beds have side rails that can be raised or lowered. These rails serve as protection for the patient and sometimes can make the patient feel more secure. There are a variety of different types of side rails designed to prevent falls, provide security for the patient, and/or provide assistance for the patient getting in and out of the bed. The side rails may or may not move with a head portion of the bed that moves upward to allow reclining by a patient.

Some embodiments herein are directed to a portable electronic device (PED) holder assembly that includes a bed connector releasably attaching the PED holder assembly to a bed side rail, for example for a hospital bed. In many embodiments, the bed connector is configured to releasably and securely mount to the side rail. In many embodiments, the PED holder assembly includes a support arm that is attached to the bed connector and to a PED holder to which a PED is attached. The support arm is, in embodiments, articulating, flexible, rotatable, and/or otherwise configurable to allow positioning of the PED holder in a desired position relative to the patient on the bed and/or hospital staff adjacent to the bed. The PED holder can be any structure that can support a PED. The PED can be any suitable portable electronic device, for example, a mobile phone, a smart phone, a personal digital assistant (PDA), a laptop computer, a desktop computer, a thin-client device, a tablet PC, an electronic book (e-book) reader, or other computing devices or electronic devices.

In some embodiments, the bed connector is designed to fit securely onto a side rail of a hospital bed so that the bed connector does not rotate relative to the side rail. In one such an embodiment, the bed connector can fit over the side rail and a bar that extends at an angle to the side rail, with the bed connector engaging both sides of the bar so that limited rotational movement of the bed connector is permitted after installation.

Turning now to the drawing figures in which the same or similar reference identifiers refer to the same or similar components throughout all of the drawing figures, FIG. 1 shows a PED holder assembly 10 for attaching a PED to hospital bed side rail 11. The PED holder assembly 10 includes a PED holder 14 to which the PED is attachable, a bed connector 16 for attaching to the bed side rail 11, and a support arm 18 extending between the bed connector 16 and the PED holder 14. In FIG. 1, the bed connector 16 is shown attached to a junction 20 at the top edge of a top rail 12 of the side rail 11 for a hospital bed. The junction 20 is the junction of the top rail 12 and a bar 22 that extends downward from the top rail 12. While suitable embodiments of the PED holder assembly 10 are described herein, U.S. patent application Ser. No. 15/705,105, entitled "Electronic Device Mount for Releasably Attaching to Equipment in a Hospital Room," which is hereby incorporated herein by reference in its entirety, provides description of a device 10 that is applicable to some embodiments of the PED holder assembly 10.

The PED holder 14 can be any suitable structure that can support a PED. For example, the PED holder 14 can include a device clamp that holds two or more sides of a PED, a stand that permits a PED to sit on top, a mount for supporting or holding a PED, one or more magnets for magnetically connecting to a PED, a tether, or any other structure that can clamp, friction fit, balance, suspend, or otherwise connect to or support a PED. The PED holder 14 can be designed to hold several different sized or shaped PEDs, and could be as simple as a flat surface. In many embodiments described herein, a PED holder assembly includes at least one assistance request button that can be pressed to communicate a request for assistance to an attendant station (e.g., a nurse station).

Figure 2:
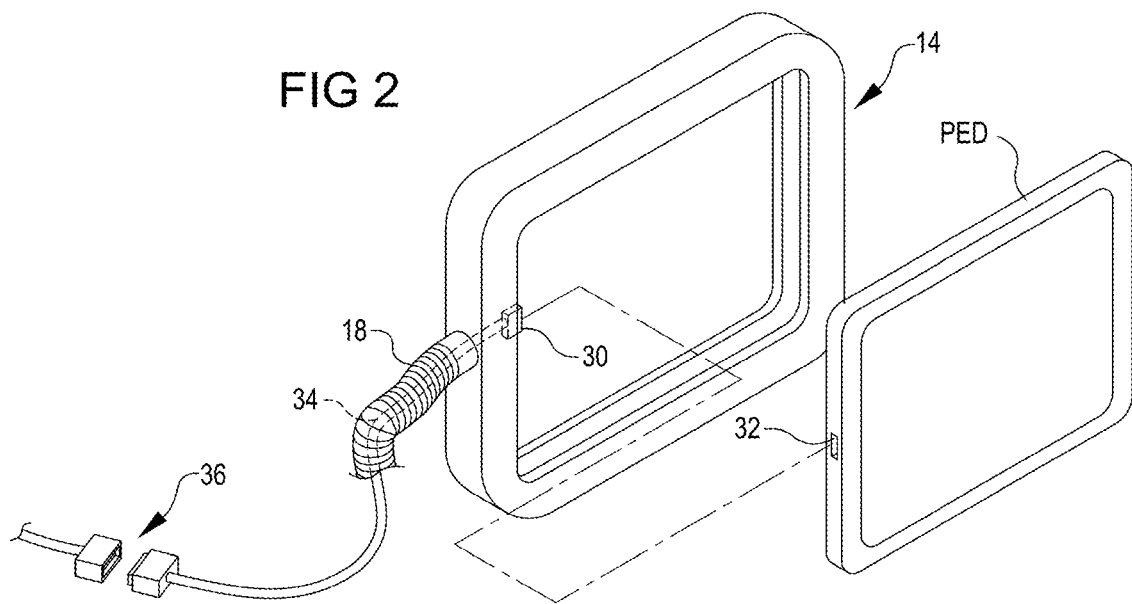
FIG. 2 shows some components of the PED holder assembly of FIG. 1.

In some embodiments, the PED holder assembly 10 include an electrical connector for providing power and/or data to the PED. In embodiments, such electrical connector includes a charging feature for fitting into a charging port or otherwise connecting to the PED to provide power and/or data to the PED. For example, as shown by FIG. 2, the PED holder 14 can include a power and/or data output connector 30 for fitting into an input port 32 of the PED. The input port 32 of the PED can have any suitable configuration and be used to supply power to the PED and/or communicate data to and/or from the PED. For example, the power and/or data output connector 30 and the input port 32 can have any suitable Universal Serial Bus (USB) configuration. In some embodiments, the PED holder assembly 10 includes a battery, such as a rechargeable battery, for charging and/or powering the PED.

Power and/or data (e.g., data for communication) can be provided to the PED through the input port 32 via the power and/or data output connector 30. In such embodiments, a wire or set of wires can extend through the support arm 18, can be wrapped around the support arm 18, or can extend from the PED holder 14 free of the support arm 18. For example, as shown in FIG. 2, a cable 34 having one or more wires extends through the support arm 18. In embodiments, the PED holder assembly 10 includes a releasable connector 36, such as a magnetic connector disclosed in U.S. Pat. No. 9,147,965 (which is hereby incorporated herein in its entirety by reference), that can be disconnected so as to permit free movement of the portion of the PED holder assembly 10 connected to the hospital bed during movement of the hospital bed or when the PED holder assembly 10 is disconnected from the hospital bed. As an alternative to a wired connection, the PED can receive communications wirelessly, and the PED can be removed for charging or replacement of batteries. In addition, cable-less charging of the PED can be provided at the PED holder 14.

The support arm 18 is, in embodiments, articulating, flexible, rotatable, and/or otherwise configurable to allow positioning of the PED holder 14 in a desired position and orientation relative to the patient. In embodiments in which the support arm 18 is movable while the bed connector 16 remains anchored to the side rail 11, the support arm 18 and the PED holder 14 can be moved to a position out of the way in an emergency, but yet the PED holder 14 is still supported by the bed connector 16 via the side rail 11. In embodiments, the support arm 18 is not only reconfigurable to vary the position and/or orientation of the PED holder 14, but also retains the PED holder 14 in a selected position and orientation, such as over a patient or out to the side of a hospital bed for access by a caregiver. To this end, the support arm 18 can include sliding, locking pieces that accommodate repositioning and reorientation of the PED holder 14 and retain a selected position and orientation of the PED holder 14, or can have a flexible nature that resists, but allows, bending along its length. For example, the support arm 18 can include flexible adjustable shafts, such as those found in gooseneck lamps. As another example, the support arm 18 can include a coiled metal tube that is reconfigurable via selective bending along the length of the coiled metal tube.

Figure 3:
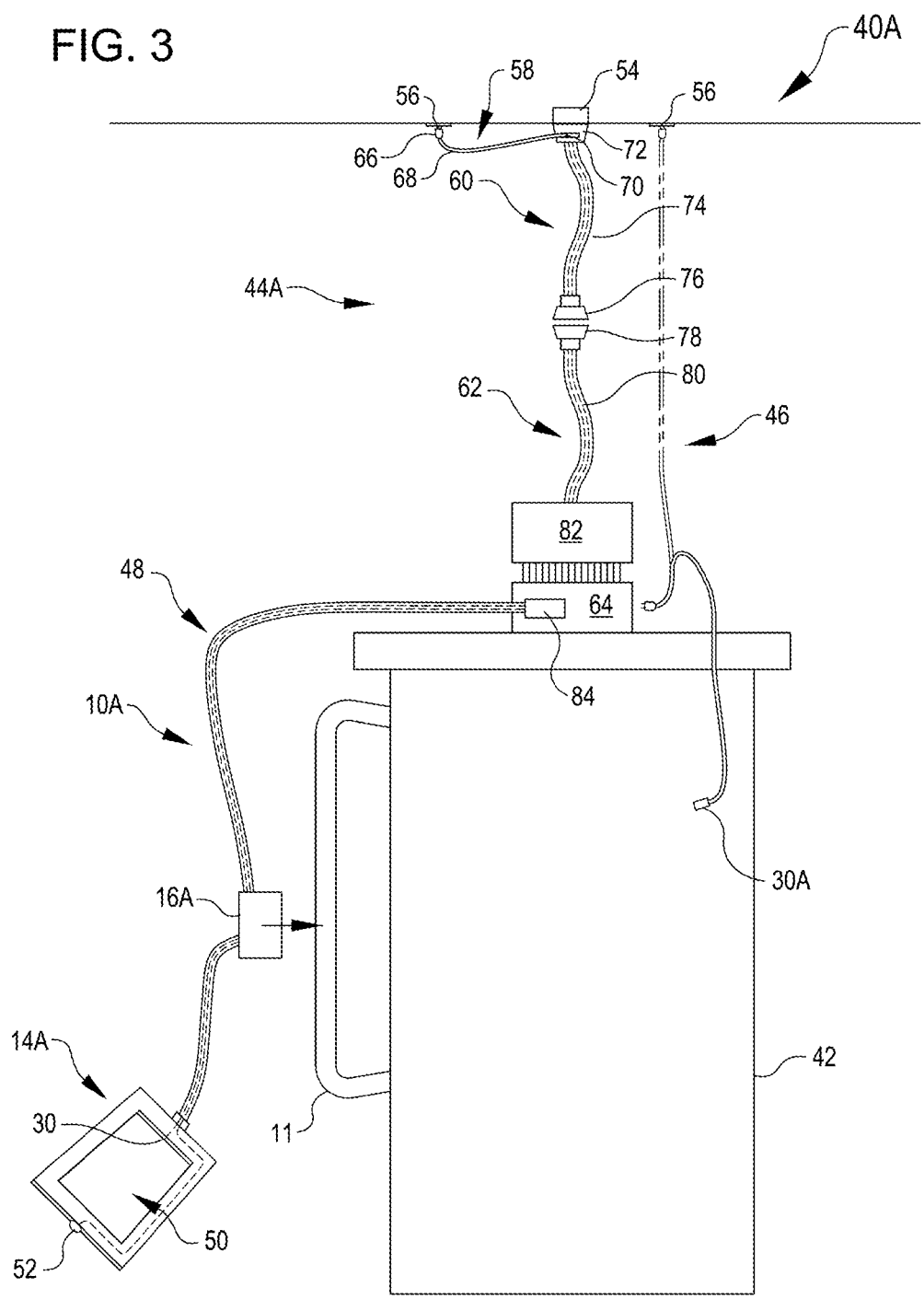
FIG. 3 shows a hospital room configuration in which a PED holder assembly is connected to a communication and power assembly for a patient bed, in accordance with embodiments.

FIG. 3 shows a hospital room configuration 40A that includes a hospital bed 42 having a side rail 11, a communication and power assembly 44A for the hospital bed 42, a PED holder assembly 10A, and, in some embodiments, a PED power and/or data cable assembly 46. The PED holder assembly 10A is configured similar to the PED holder assembly 10. For example, reference identifiers associated with components of PED holder assembly 10A that are the same or similar to components of the PED holder assembly 10 are the same or similar to reference identifiers associated with the components of the PED holder assembly 10. The PED holder assembly 10A includes a PED holder 14A, a bed connector 16A, and a power and/or data cable assembly 48. The PED holder 14A has a recess 50 shaped and sized to accommodate and hold a PED placed in the recess 50. In some embodiments, the PED holder 14A includes suitable retention features that retain the PED in the recess 50 to prevent inadvertent detachment of the PED from the PED holder 14A and accommodate intentional removal of the PED from the PED holder 14A. The PED holder 14A includes a power and/or data output connector 30 for fitting into an input port 32 of a PED held by the PED holder 14A. The PED holder 14A further includes a assistance request button 52 that can be pressed to communicate a request for assistance to an attendant station. The power and/or data cable assembly 48 operatively connects the power and/or data output connector 30 to the communication and power assembly 44A. The bed connector 16A is attachable to the side rail 11. The bed connector 16A is attached to, or attachable to, the power and/or data cable assembly 48 to retain the power and/or data cable assembly 48 within reach of a patient in the bed 42. In some embodiments, the distal end of the cable assembly 48 is securely attached to the PED holder 14A so that the patient can grab and pull on the cable assembly 48 to bring the PED holder 14A within reach of the patient when the patient wants to use the PED and/or press the assistance request button 52 to request assistance. In some embodiments, the PED holder assembly 10A includes a support arm the same as, or similar to, the support arm 18 of the PED holder assembly 10 to support the PED holder 14A in a selected position and orientation relative to the bed connector 16A.

In some embodiments, the communication and power assembly 44A operatively connects the bed 42 to a assistance request communication system hub 54 and connects the PED holder assembly 10A to a power and/or data outlet 56. The assistance request communication system hub 54 is operatively connected to a assistance request communication system that is operable to transmit a assistance request signal generated via operation of the assistance request button 52 to an attendant station. The power and/or data outlet 56 supplies power and/or data to a PED held by the PED holder assembly 10A through the communication and power assembly 44A and the cable assembly 48. The communication and power assembly 44A includes a PED power and/or data cable assembly 58, a proximal cable assembly 60, a distal cable assembly 62, and an intermediate connector 64 mounted to the bed 42. The PED power and/or data cable assembly 58 includes a proximal connector 66, a power and/or data cable 68, and a distal connector 70. The proximal cable assembly 60 includes a proximal connector 72, a power/communication cable 74, and a distal connector 76. The distal cable assembly 62 includes a proximal connector 78, a power/communication cable 80, and a distal connector 82. The proximal connector 66 of the cable assembly 58 is connectable to the power and/or data outlet 56 and the distal connector 70 of the cable assembly 58 is connectable to the proximal connector 72 of the cable assembly 60 to operatively connect the communication and power assembly 44A to the power and/or data outlet 56. The proximal connector 72 of the cable assembly 60 is connectable to the hub 54 to operatively connect the communication and power assembly 44A to the assistance request communication system. The proximal connector 78 of the cable assembly 62 is connectable to the distal connector 76 of the cable assembly 60 to operatively connect the cable assembly 62 to the assistance request communication system and the outlet 56. The distal connector 82 of the cable assembly 62 is connectable to the intermediate connector 64 to operatively connect the intermediate connector 64 to the assistance request communication system and the power and/or data outlet 56. The power and/or data cable assembly 48 includes a proximal connector 84 that is connectable to the intermediate connector 64 to operatively connect the power and/or data cable assembly 48 to the assistance request communication system and the outlet 56.

In some embodiments, the communication and power assembly 44A operatively connects the intermediate connector 64 to the assistance request communication system hub 54 and the intermediate connector 64 is operatively connected to a power and/or data outlet 56 via the PED power and/or data cable assembly 46. In the illustrated embodiment, the PED power and/or data cable assembly 46 includes a distal power and/or data output connector 30A, which can be connected to an input port 32 of a PED to operatively connect the PED to the power and/or data outlet 56.

In some embodiments, the communication and power assembly 44A is configured to enable quick disconnection of the bed 42 from the assistance request communication system hub 54 and the power and/or data outlet 56 when the bed 42 needs to be moved. For example, the distal connector 76 and the proximal connector 78 can form a releasable magnetic connection, such as the magnetic connector disclosed in U.S. Pat. No. 9,147,965. As another example, the distal connector 82 and the intermediate connector 64 can form a releasable magnetic connection, such as the magnetic connector disclosed in U.S. Pat. No. 9,147,965.

Figure 4:
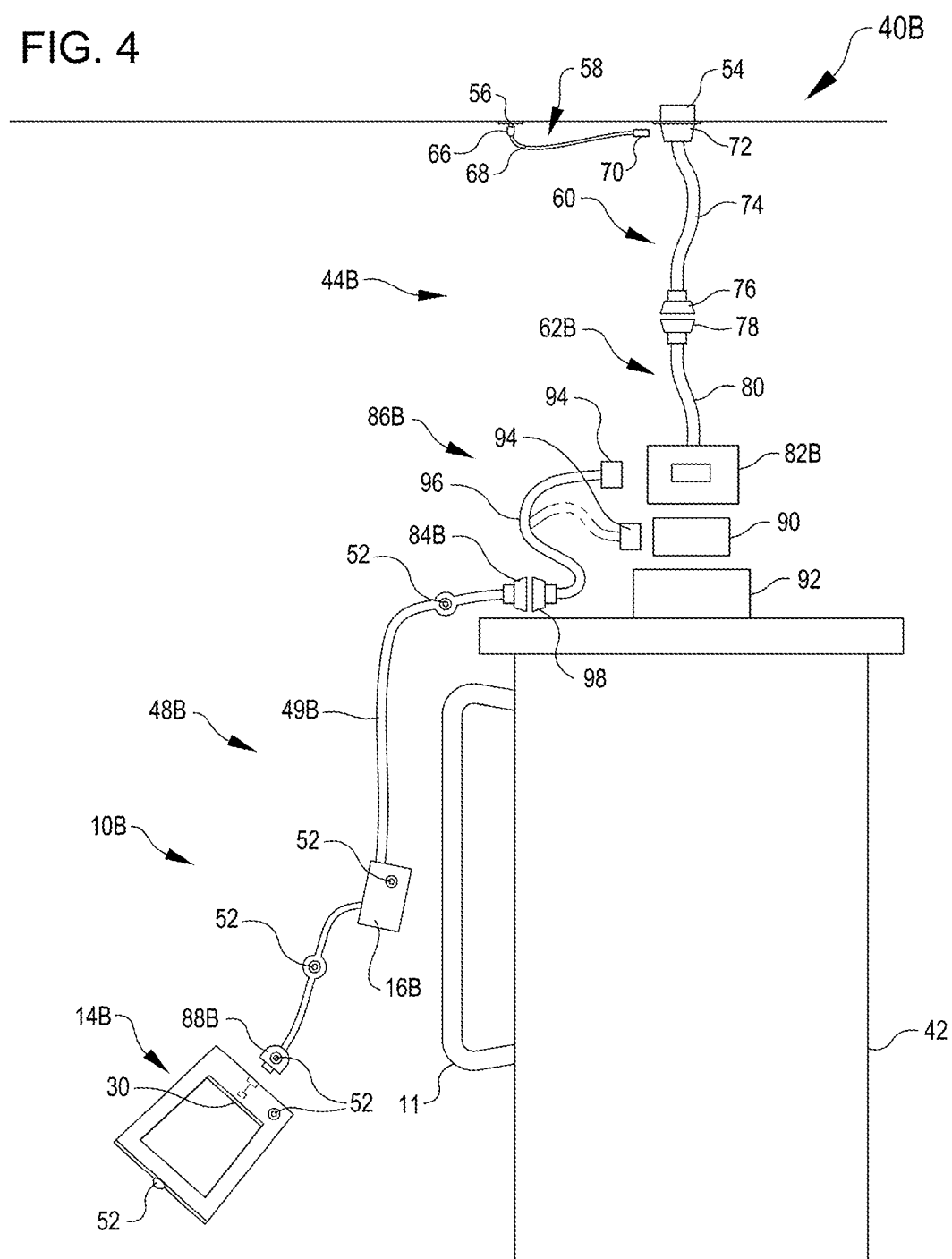
FIG. 4 shows a hospital room configuration in which a PED holder assembly is connected to a communication and power assembly for a patient bed, in accordance with embodiments, the PED holder assembly including one or more assistance request buttons.

FIG. 4 shows a hospital room configuration 40B that includes a hospital bed 42 having a side rail 11, a communication and power assembly 44B for the hospital bed 42, an intermediate connector assembly 86B, and a PED holder assembly 10B. The PED holder assembly 10B is configured similar to the PED holder assembly 10. For example, reference identifiers associated with components of PED holder assembly 10B that are the same or similar to components of the PED holder assembly 10 are the same or similar to reference identifiers associated with the components of the PED holder assembly 10. The PED holder assembly 10B includes a PED holder 14B, a bed connector 16B, and a power and/or data cable assembly 48B. The PED holder 14B has a recess 50 shaped and sized to accommodate and hold a PED placed in the recess 50. In some embodiments, the PED holder 14B includes suitable retention features that retain the PED in the recess 50 to prevent inadvertent detachment of the PED from the PED holder 14B and accommodate intentional removal of the PED from the PED holder 14B. The PED holder 14B includes a power and/or data output connector 30 for fitting into an input port 32 of a PED held by the PED holder 14B. The PED holder 14B can include any suitable number of assistance request buttons 52 that can be pressed to communicate a request for assistance to an attendant station. For example, in the illustrated embodiment, the PED holder 14B includes two assistance request buttons 52. The power and/or data cable assembly 48B operatively connects the power and/or data output connector 30 and the assistance request buttons 52 to the intermediate cable assembly 86B. The power and/or data cable assembly 48B can include any suitable number of assistance request buttons 52 that can be pressed to communicate a request for assistance to an attendant station. For example, in the illustrated embodiment, the power and/or data cable assembly 48B includes three assistance request buttons 52 distributed along the length of the power and/or data cable assembly 48B. The power and/or data cable assembly 48B includes a distal connector 88B that is connectable to the PED holder 14B to operatively couple the PED holder 14B to the power and/or data cable assembly 48B. In the illustrated embodiment, the distal connector 88B includes a assistance request buttons 52 that can be pressed to communicate a request for assistance to an attendant station. The bed connector 16B is attachable to the side rail 11. The bed connector 16B is attached to, or attachable to, the power and/or data cable assembly 48B to retain the power and/or data cable assembly 48B within reach of a patient in the bed 42 so that the patient can grab and pull on the cable assembly 48 to bring the PED holder 14B within reach of the patient when the patient wants to use the PED and/or press the assistance request button 52 to request assistance. In some embodiments, the PED holder assembly 10B includes a support arm the same as, or similar to, the support arm 18 of the PED holder assembly 10 to support the PED holder 14B in a selected position and orientation relative to the bed connector 16B.

The communication and power assembly 44B operatively connects the intermediate cable assembly 86B to the assistance request communication system hub 54 and the outlet 56 and connects the bed 42 to the assistance request communication system hub 54 and, in some embodiments, the outlet 56. The power and/or data outlet 56 supplies power and/or data to a PED held by the PED holder assembly 10B through the communication and power assembly 44B, the intermediate cable assembly 86B, and the cable assembly 48B. The communication and power assembly 44B includes the PED power and/or data cable assembly 58, the proximal cable assembly 60, a distal cable assembly 62B, and a coupler 90. The distal cable assembly 62B includes the proximal connector 78, the power/communication cable 80, and a distal connector 82B. The proximal connector 66 of the cable assembly 58 is connectable to the outlet 56 and the distal connector 70 of the cable assembly 58 is connectable to the proximal connector 72 of the cable assembly 60 to operatively connect the communication and power assembly 44B to the power and/or data outlet 56. The proximal connector 72 of the cable assembly 60 is connectable to the assistance request hub 54 to operatively connect the communication and power assembly 44B to the assistance request communication system. The proximal connector 78 of the cable assembly 62B is connectable to the distal connector 76 of the cable assembly 60 to operatively connect the cable assembly 62B to the assistance request communication system and the outlet 56. The distal connector 82B of the cable assembly 62 is connectable to the coupler 90 to operatively connect the coupler 90 to the assistance request communication system and the outlet 56.

The bed 42 includes a bed hub 92 to which the coupler 90 is connectable to operatively connect the bed hub 92 to the assistance request communication system and/or the outlet 56. In some embodiments, the bed 42 includes any suitable number of assistance request buttons 52 that are operatively coupled with the assistance request communication system via the bed hub 92.

The intermediate cable assembly 86B operatively connects the PED holder assembly 10B to the assistance request communication system hub 54 and the outlet 56. The intermediate cable assembly 86B includes a proximal connector 94, a cable 96 operatively connected to the proximal connector 94, and a distal connector 98 operatively connected to the cable 96. In some embodiments, the proximal connector 94 is connectable to the distal connector 82B to operatively connect the intermediate cable assembly 86 to the assistance request communication system and the outlet 56 via the communication and power assembly 44B. In some embodiments, the proximal connector 94 is connectable to the coupler 90 to operatively connect the intermediate cable assembly 86 to the assistance request communication system and the outlet 56 via the communication and power assembly 44B.

The cable assembly 48B operatively connects the PED holder 14B to the assistance request communication system hub 54 and the outlet 56. The cable assembly 48B includes a proximal connector 84B, a cable 49B operatively connected to the proximal connector 84B, and the distal connector 88B operatively connected to the cable 49B. The proximal connector 84B is connectable to the distal connector 98 to operatively connect the cable assembly 48B to the assistance request communication system and the outlet 56 via the intermediate cable assembly 86B and the communication and power assembly 44B.

The hospital room configuration 40B can include any suitable number of quick disconnection features that enhance the ability to move the bed 42 and/or the PED holder assembly 10B. For example, in some embodiments, the distal connector 76 and the proximal connector 78 form a quick release connection, such as the magnetic connector disclosed in U.S. Pat. No. 9,147,965. In some embodiments, the distal connector 98 and the proximal connector 84B form a quick release connection, such as the magnetic connector disclosed in U.S. Pat. No. 9,147,965.

Figure 5:
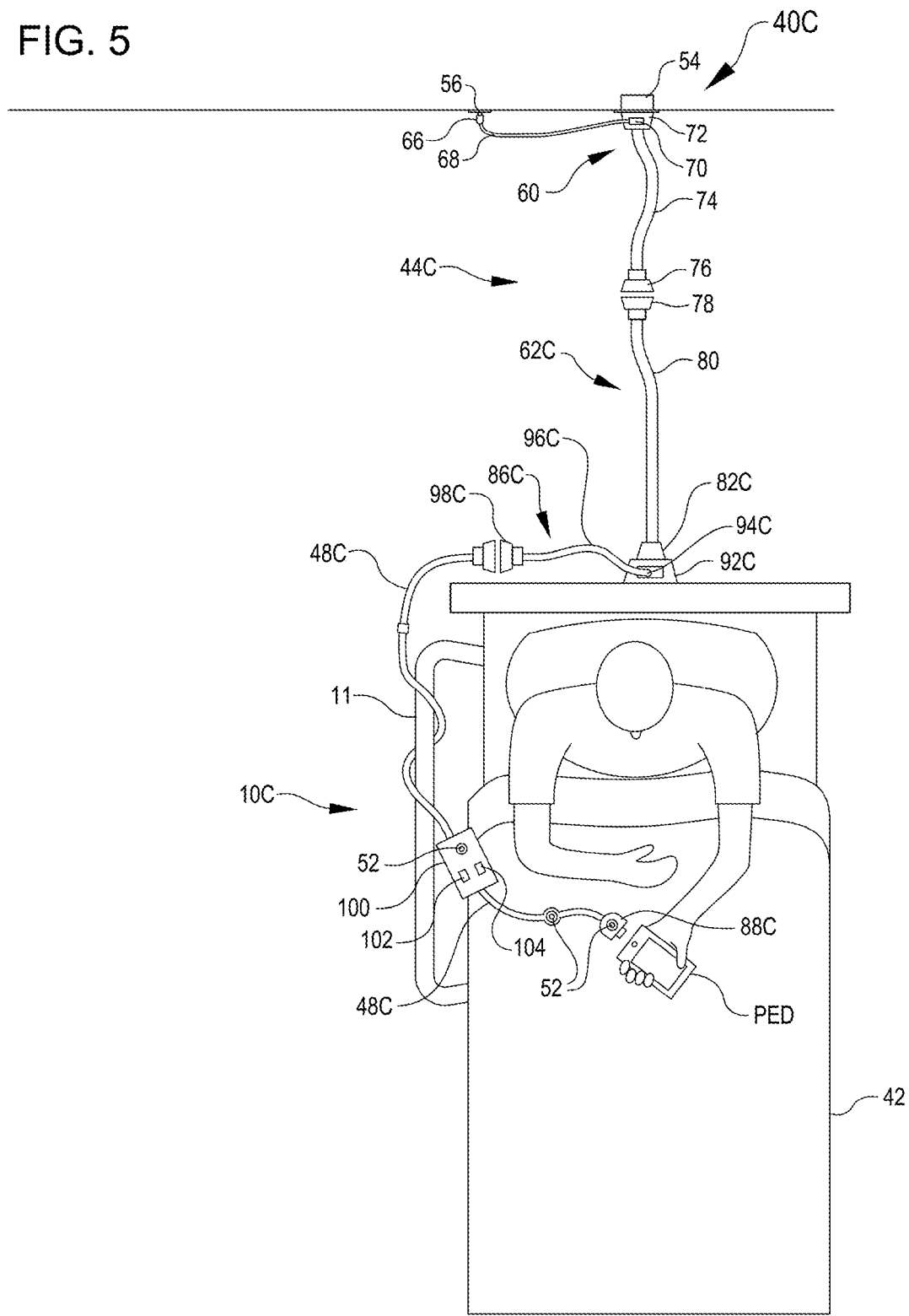
FIG. 5 shows a hospital room configuration in which a communication and power assembly for use by a patient is connected to a communication and power assembly for a patient bed, in accordance with embodiments.

FIG. 5 shows a hospital room configuration 40C that includes a hospital bed 42 having a side rail 11, a communication and power assembly 44C for the hospital bed 42, an intermediate connector assembly 86C, and a assistance request/PED cable assembly 10C. The assistance request/PED cable assembly 10C is configured similar to the PED holder assembly 10B, but without the PED holder 14B. For example, reference identifiers associated with components of assistance request/PED cable assembly 10C that are the same or similar to components of the PED holder assembly 10B are the same or similar to reference identifiers associated with the components of the PED holder assembly 10B. The assistance request/PED cable assembly 10C includes a proximal connector 84C, a cable assembly 48C, a patient interface unit 100, and a distal connector 88C. The distal connector 88C is a power and/or data output connector for fitting into an input port 32 of a PED. The distal connector 88C operatively connects the PED to the assistance request/PED cable assembly 10C. The cable assembly 48C can include any suitable number of assistance request buttons 52 that can be pressed to communicate a request for assistance to an attendant station. For example, in the illustrated embodiment, the cable assembly 48C includes one assistance request button located between the patient interface unit 100 and the distal connector 88C. The distal connector 88C also includes a assistance request buttons 52 that can be pressed to communicate a request for assistance to an attendant station. The patient interface unit 100 includes a assistance request button 52 and can include any suitable patient input devices, such as a remote control input devices for a television. In some embodiments, the cable assembly 48C can be wrapped around the side rail 11 to retain the cable assembly 48C within reach of a patient in the bed 42 when the patient wants to use the PED and/or press the assistance request button 52 to request assistance.

The communication and power assembly 44C operatively connects the intermediate cable assembly 86C to the assistance request communication system hub 54 and the outlet 56 and connects the bed 42 to the assistance request communication system hub 54 and, in some embodiments, the outlet 56. The power and/or data outlet 56 supplies power and/or data to a PED connected to the assistance request/PED cable assembly 10C through the communication and power assembly 44C, the intermediate cable assembly 86C, and the cable assembly 48C. The communication and power assembly 44C includes the PED power and/or data cable assembly 58, the proximal cable assembly 60, and a distal cable assembly 62C. The distal cable assembly 62C includes the proximal connector 78, the power/communication cable 80, and a distal connector 82C. The proximal connector 66 of the cable assembly 58 is connectable to the outlet 56 and the distal connector 70 of the cable assembly 58 is connectable to the proximal connector 72 of the cable assembly 60 to operatively connect the communication and power assembly 44C to the power and/or data outlet 56. The proximal connector 72 of the cable assembly 60 is connectable to the hub 54 to operatively connect the communication and power assembly 44C to the assistance request communication system. The proximal connector 78 of the cable assembly 62C is connectable to the distal connector 76 of the cable assembly 60 to operatively connect the cable assembly 62C to the assistance request communication system and the outlet 56. The bed 42 includes a bed hub 92C to which the distal connector 82C is connectable to operatively connect the bed hub 92C to the assistance request communication system and/or the outlet 56. In some embodiments, the bed 42 includes any suitable number of assistance request buttons 52 that are operatively coupled with the assistance request communication system via the bed hub 92C.

The intermediate cable assembly 86C operatively connects the assistance request/PED cable assembly 10C to the assistance request communication system hub 54 and the outlet 56 via the communication and power assembly 44C. The intermediate cable assembly 86C includes a proximal connector 94C, a cable 96C operatively connected to the proximal connector 94C, and a distal connector 98C operatively connected to the cable 96C. The proximal connector 94C is connectable to the bed hub 92C to operatively connect the intermediate cable assembly 86C to the assistance request communication system and the outlet 56 via the communication and power assembly 44C.

The hospital room configuration 40C can include any suitable number of quick disconnection features that enhance the ability to move the bed 42 and/or the assistance request/PED cable assembly 10C. For example, in some embodiments, the distal connector 76 and the proximal connector 78 form a quick release connection, such as the magnetic connector disclosed in U.S. Pat. No. 9,147,965. In some embodiments, the distal connector 98C and the proximal connector 84C form a quick release connection, such as the magnetic connector disclosed in U.S. Pat. No. 9,147,965.

Figure 6:
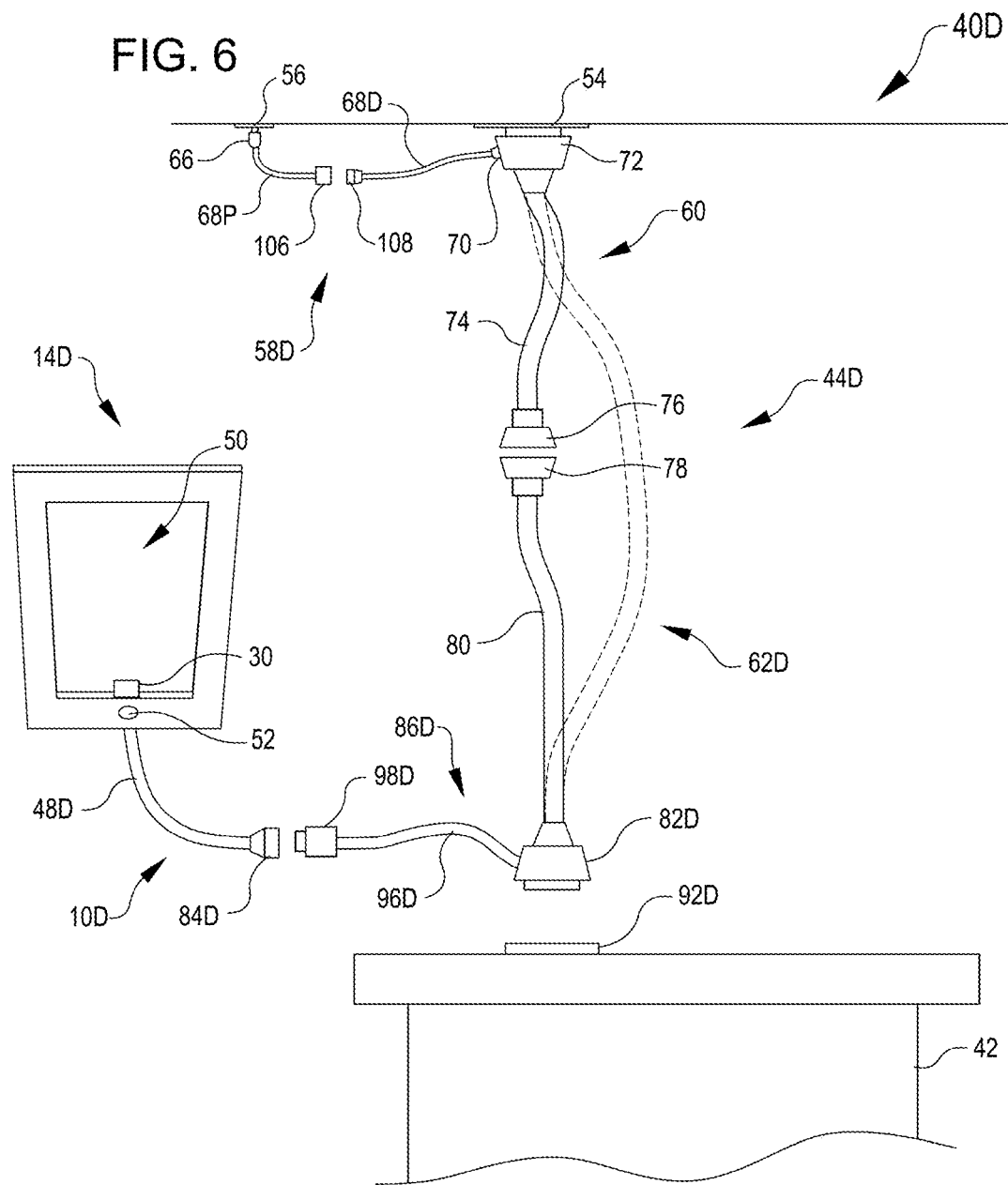
FIG. 6 shows a hospital room configuration in which a PED holder assembly is connected to a communication and power assembly for a patient bed, in accordance with embodiments, the PED holder assembly including a assistance request button.

FIG. 6 shows a hospital room configuration 40D that includes a hospital bed 42, a communication and power assembly 44D for the hospital bed 42, and a PED holder assembly 10D. The communication and power assembly 44D is configured similar to the communication and power assembly 44C, but including an intermediate connector assembly 86D that is integral to the distal cable assembly 62C. For example, reference identifiers associated with components of the communication and power assembly 44D that are the same or similar to components of the communication and power assembly 44C are the same or similar to reference identifiers associated with the components of the communication and power assembly 44C. The PED holder assembly 10D includes a proximal connector 84D, a cable assembly 48D, and a PED holder 14D. The PED holder assembly 10D is configured similar to the PED holder assembly 10. For example, reference identifiers associated with components of PED holder assembly 10D that are the same or similar to components of the PED holder assembly 10 are the same or similar to reference identifiers associated components of the PED holder assembly 10. The PED holder 14D can include any suitable number of assistance request buttons 52 that can be pressed to communicate a request for assistance to an attendant station. For example, in the illustrated embodiment, the PED holder 14D includes a single assistance request button 52.

The communication and power assembly 44D operatively connects the PED holder assembly 10D to the assistance request communication system hub 54 and the outlet 56 and connects the bed 42 to the assistance request communication system hub 54 and, in some embodiments, the outlet 56. The power and/or data outlet 56 supplies power and/or data to a PED held by the PED holder 14D through the communication and power assembly 44D. The communication and power assembly 44D includes a PED power and/or data cable assembly 58D, the proximal cable assembly 60, and a distal cable assembly 62D. The distal cable assembly 62D includes the proximal connector 78, the power/communication cable 80, a distal connector 82D, and the intermediate connector assembly 86D. The PED power and/or data cable assembly 58D includes the proximal connector 66, a proximal cable 68P, a connector 106, a connector 108, a distal cable 68D, and the distal connector 70. The proximal connector 66 is connectable to the outlet 56, the connector 108 is connectable to the connector 106, and the distal connector 70 is connectable to the proximal connector 72 of the cable assembly 60 to operatively connect the communication and power assembly 44D to the power and/or data outlet 56. The proximal connector 72 of the cable assembly 60 is connectable to the assistance request hub 54 to operatively connect the communication and power assembly 44D to the assistance request communication system. The proximal connector 78 of the cable assembly 62D is connectable to the distal connector 76 of the cable assembly 60 to operatively connect the cable assembly 62D to the assistance request communication system and the outlet 56. The bed 42 includes a bed hub 92D to which the distal connector 82D is connectable to operatively connect the bed hub 92D to the assistance request communication system and/or the outlet 56. In some embodiments, the bed 42 includes any suitable number of assistance request buttons 52 that are operatively coupled with the assistance request communication system via the bed hub 92D. In some embodiments of the communication and power assembly 44D, the connectors 76, 78 are omitted and a single cable segment connects the connectors 72, 82D.

The intermediate cable assembly 86D operatively connects the PED holder assembly 10D to the assistance request communication system hub 54 and the outlet 56. The intermediate cable assembly 86C includes a cable 96D and a distal connector 98D operatively connected to the cable 96C. The cable 96D is operatively connected to the connector 82D and extends from the connector 82D.

The hospital room configuration 40D can include any suitable number of quick disconnection features that enhance the ability to move the bed 42 and/or the PED holder assembly 10D. For example, in some embodiments, the distal connector 76 and the proximal connector 78 form a quick release connection, such as the magnetic connector disclosed in U.S. Pat. No. 9,147,965. In some embodiments, the distal connector 98D and the proximal connector 84D form a quick release connection, such as the magnetic connector disclosed in U.S. Pat. No. 9,147,965.

Figure 7:
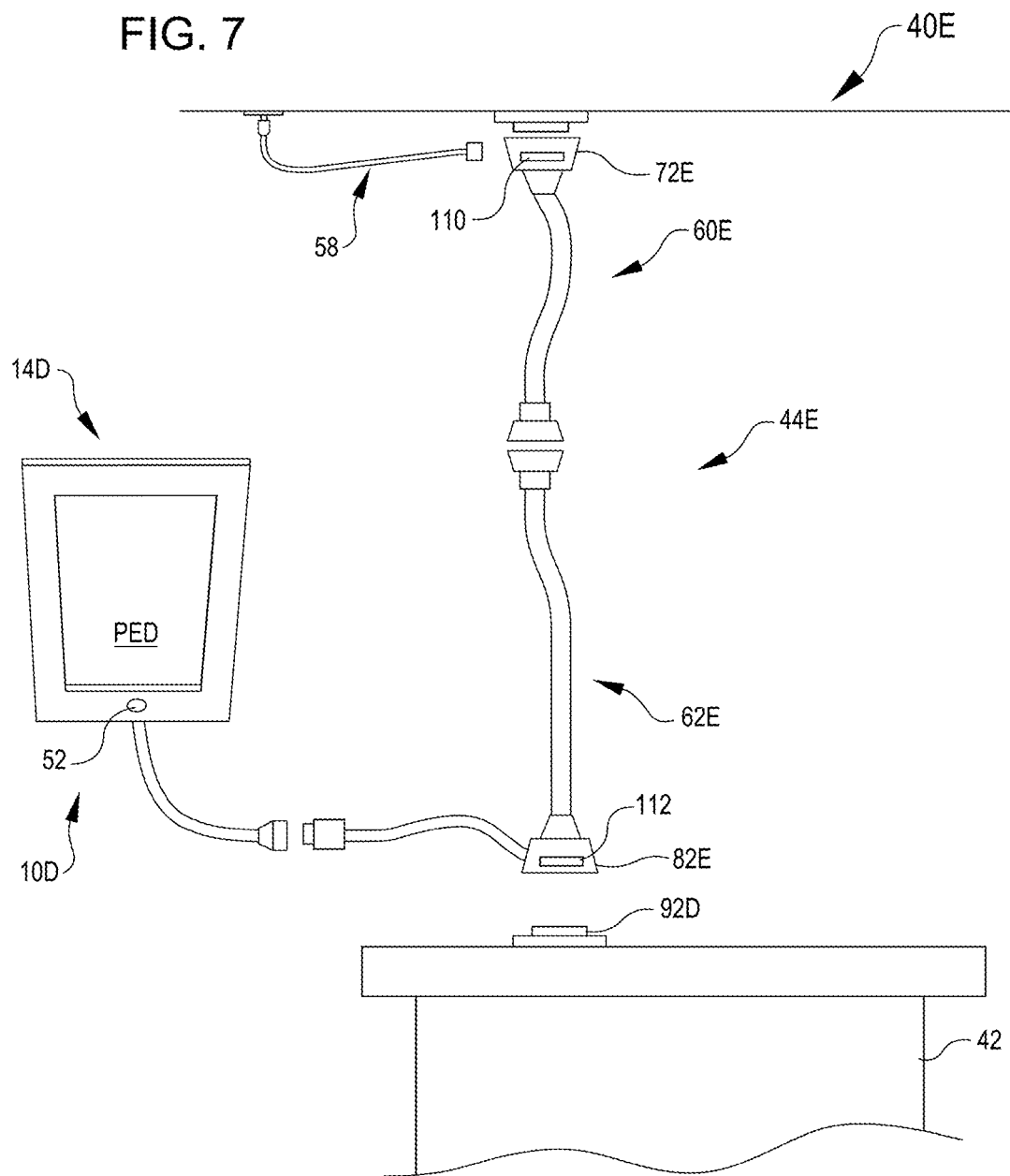
FIG. 7 shows a hospital room configuration in which a PED holder assembly is connected to a communication and power assembly for a patient bed, in accordance with embodiments, the PED holder assembly including a assistance request button.

FIG. 7 shows a hospital room configuration 40E that is similar to the hospital room configuration 40D except for differences described below. Reference identifiers associated with components of the hospital room configuration 40E that are the same or similar to components of the hospital room configuration 40D are the same or similar to reference identifiers associated with the components of the hospital room configuration 40D. The hospital room configuration 40E includes the one-piece PED power and/or data cable assembly 58 shown in FIG. 4 as opposed to the two-piece PED power and/or data cable assembly 58D shown in FIG. 6. The hospital room configuration 40E employs a communication and power assembly 44E as opposed to the communication and power assembly 44D shown in FIG. 6. The communication and power assembly 44E includes a proximal cable assembly 60E and a distal cable assembly 62E. The proximal cable assembly 60E is similar to the proximal cable assembly 60D, but has a proximal connector 72E that includes a power/data output port 110 to which a PED can be connected via a suitable connection cable. The distal cable assembly 62E is similar to the distal cable assembly 62E, but has a distal connector 82E that includes a power/ data output port 112 to which a PED can be connected via a suitable connection cable.

Figure 8:
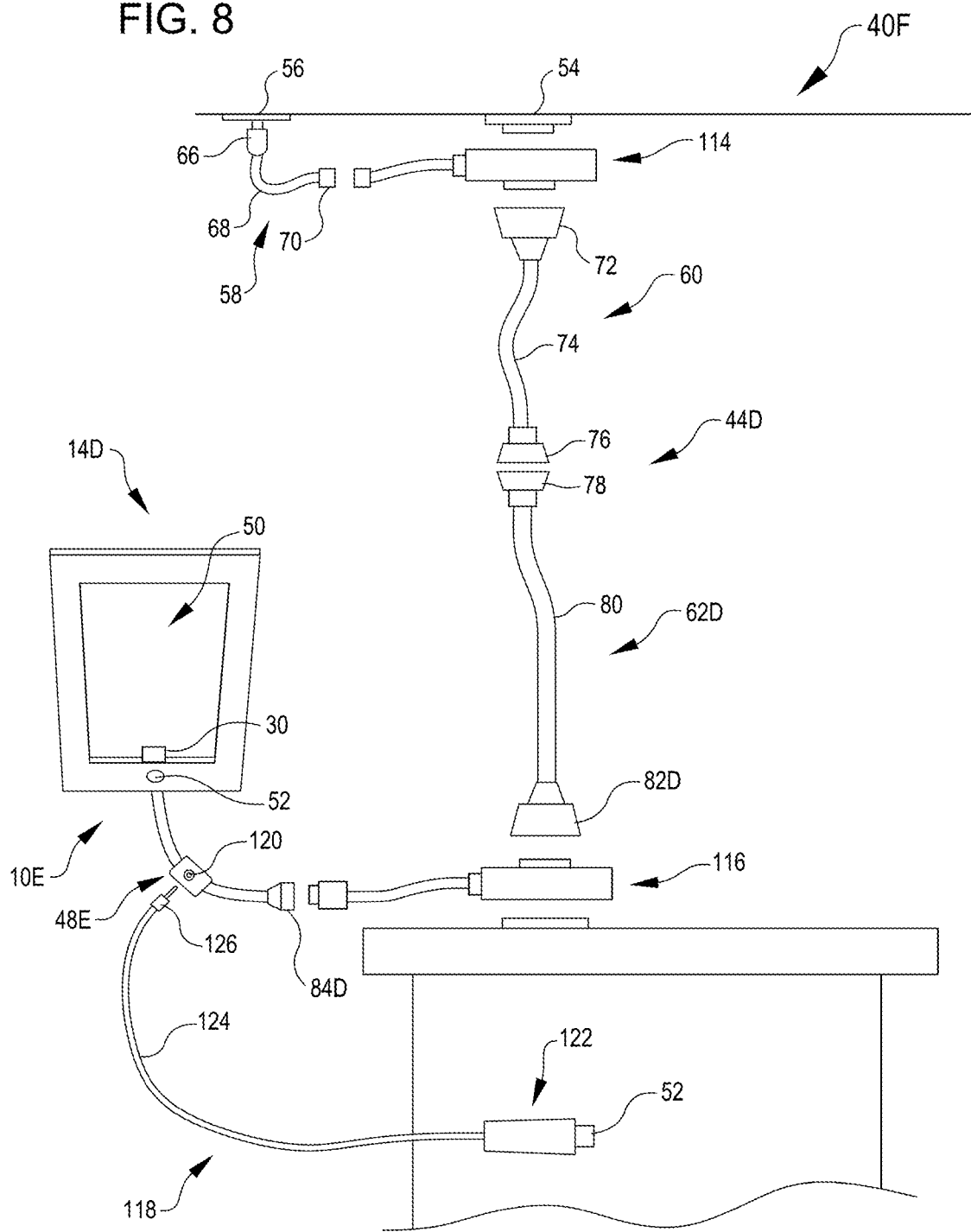
FIG. 8 shows a hospital room configuration in which a PED holder assembly is connected to a communication and power assembly for a patient bed, in accordance with embodiments, the PED holder assembly including a connection port for a assistance request button assembly.

FIG. 8 shows a hospital room configuration 40F that is similar to the hospital room configuration 40D except for differences described below. Reference identifiers associated with components of the hospital room configuration 40F that are the same or similar to components of the hospital room configuration 40D are the same or similar to reference identifiers associated with the components of the hospital room configuration 40D. The hospital room configuration 40F includes a proximal coupler 114 and a distal coupler 116. The proximal coupler 114 is connectable to and between the proximal connector 72 and the assistance request hub 54 to operatively couple the communication and power assembly 44D to the assistance request hub 54. Additionally, the proximal coupler 114 operatively couples the communication and power assembly 44D to the PED power and/or data cable assembly 58. The distal coupler 116 is connectable to and between the distal coupler 82D and the bed hub 92D to operatively coupled the bed 42 to the assistance request hub 54, and in some embodiments, to the power and/or data outlet 56. Additionally, the distal coupler 116 is connectable to and between the distal coupler 82D and the proximal connector 84D of the PED holder assembly 10E to operatively couple the PED holder assembly 10E to the assistance request hub 54 and the power and/or data outlet 56. The PED holder assembly 10E is configured similar to the PED holder assembly 10D shown in FIG. 6, but includes a assistance request cable assembly 118 and a connection port 120 to which the assistance request cable assembly 118 can be operatively connected to the assistance request hub 54. The assistance request cable assembly 118 includes a assistance request button assembly 122, a cable 124, and a proximal connector 126 connected to the assistance request button assembly 112 by the cable 124. The assistance request button assembly 122 includes a assistance request button 52 that can be pressed by a patient to communicate a request for assistance to an attendant station.

The hospital room configuration 40F can include any suitable number of quick disconnection features that enhance the ability to move the bed 42 and/or the PED holder assembly 10E. For example, in some embodiments, the distal connector 76 and the proximal connector 78 form a quick release connection, such as the magnetic connector disclosed in U.S. Pat. No. 9,147,965. In some embodiments, the proximal coupler 114 forms part of a quick release connection, such as the magnetic connector disclosed in U.S. Pat. No. 9,147,965. In some embodiments, the distal coupler 116 forms part of a quick release connection, such as the magnetic connector disclosed in U.S. Pat. No. 9,147,965.

Figure 9:
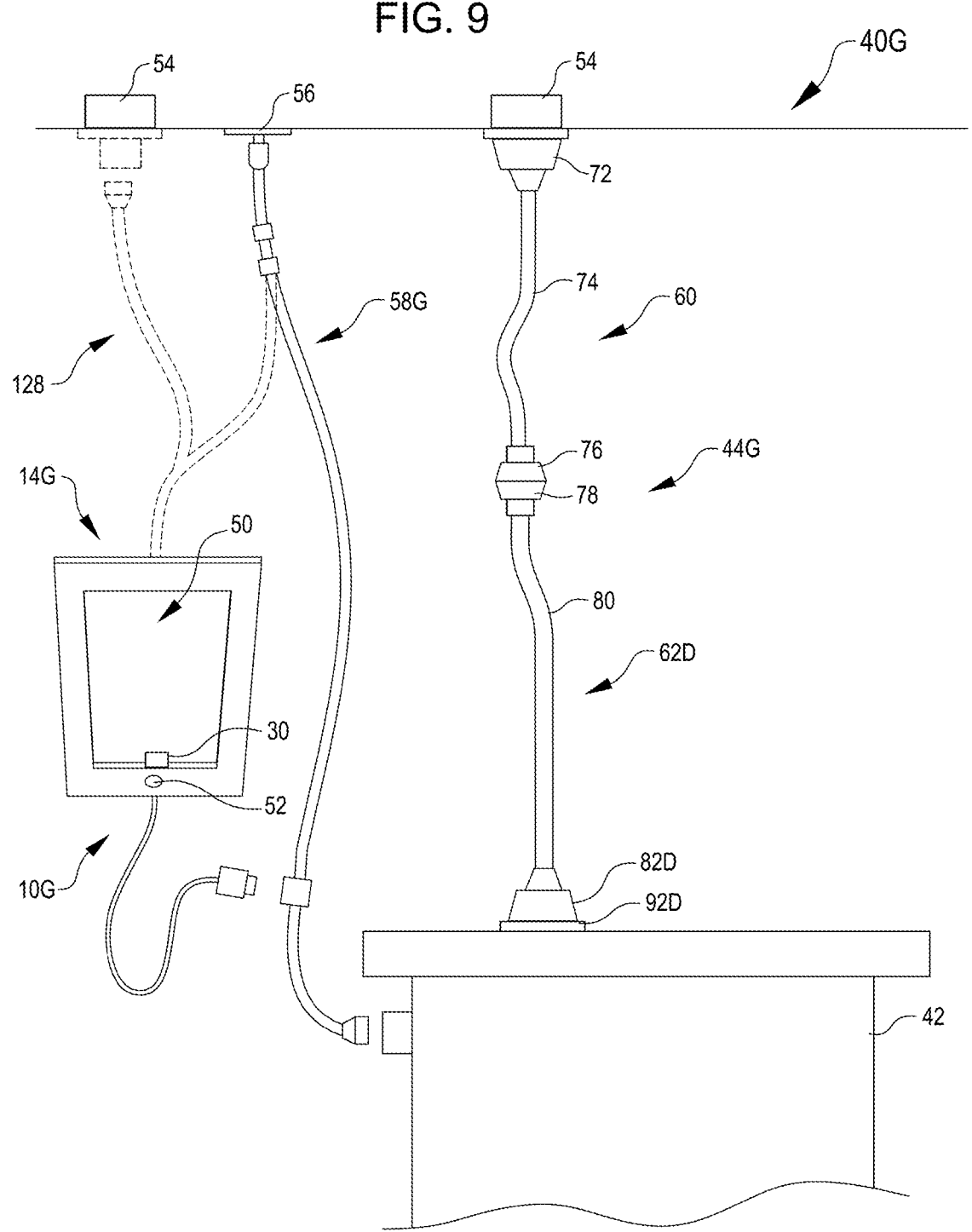
FIG. 9 shows a hospital room configuration that includes a PED holder assembly that can be connected to a communication and power assembly for a patient bed or connected directly to a power and/or data device that supplies power and/or data to a PED, in accordance with embodiments, the PED holder assembly including a assistance request button.

FIG. 9 shows a hospital room configuration 40G in which the bed 42 is coupled to the assistance request hub 54 via a assistance request communication cable assembly 44G. In some embodiments, the bed 42 is separately coupled to a power and/or data output 56 via a cable assembly 58G. The configuration 40G includes a PED holder assembly 10G, which in some embodiments is configured the same as the PED holder assembly 10D shown in FIG. 6 and be operatively connectable to the power and/or data output 56 through the cable assembly 58G and to the assistance request hub 54 through a communication path that includes the cable assembly 58G, the bed 42, and the assistance request communication cable assembly 44G. In an alternate embodiment, the PED holder assembly 10G includes a connection cable assembly 128 that operatively couples the PEG holder assembly 10G to a assistance request hub 54 and the power and/or data output 56.

Figure 10:
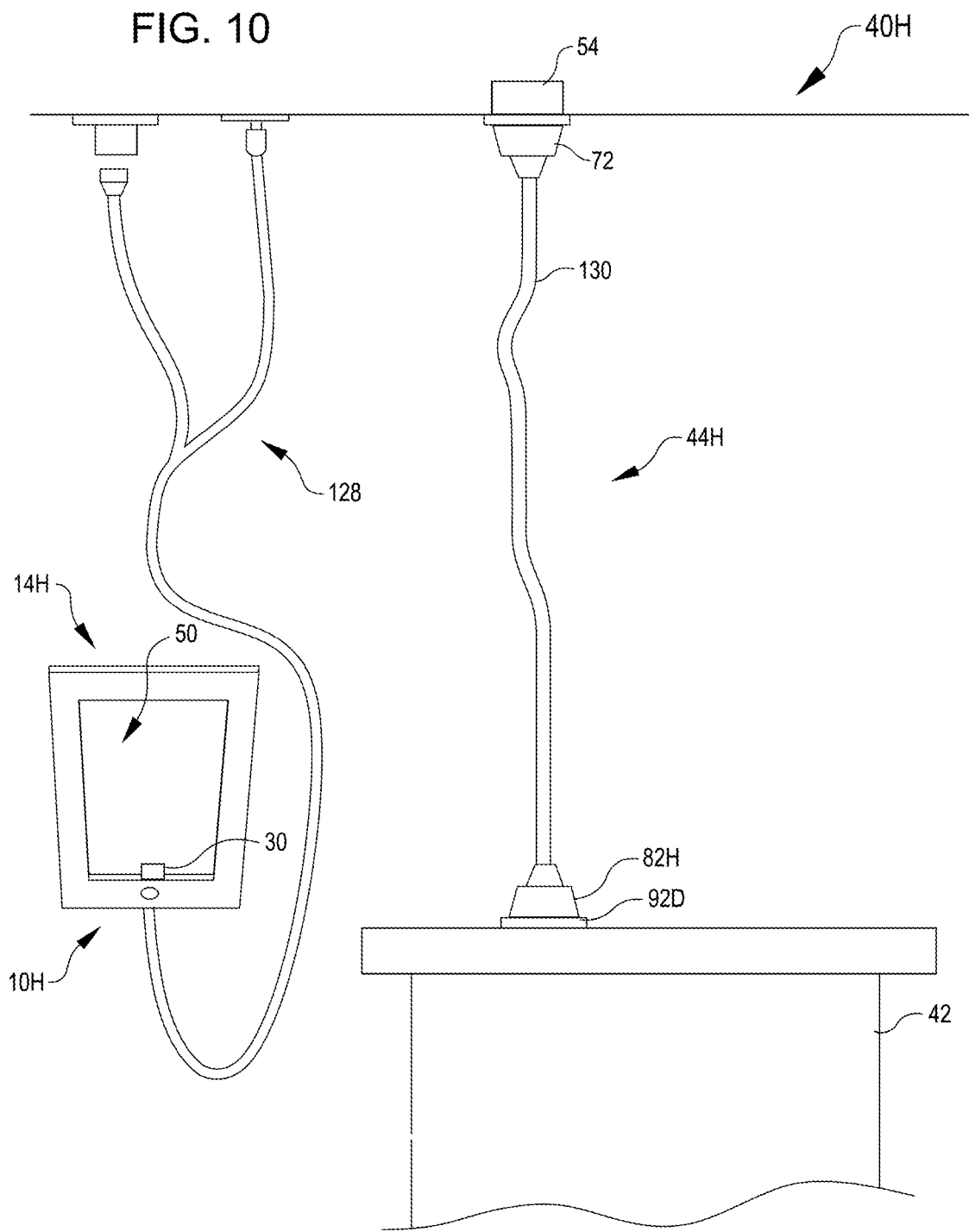
FIG. 10 shows a hospital room configuration that includes a PED holder assembly connected directly to a power and/or data device that supplies power and/or data to a PED, in accordance with embodiments, the PED holder assembly including a assistance request button.

FIG. 10 shows a hospital room configuration 40H that is similar to the hospital room configuration 40G shown in FIG. 9 except for differences described below. In the hospital room configuration 40H, the bed 42 is coupled to a assistance request hub 54 via a assistance request communication cable assembly 44H and a PED holder assembly 10H is coupled to a assistance request hub 54 and the power and/or data outlet 56 without being connected to the assistance request communication cable assembly 44H or the bed 42. The PED holder assembly 10H includes a PED holder 14H (which is configured similar to the PED holder 14D) and the connection cable assembly 128, which is connectable to each of a assistance request hub 54 and the power and/or data outlet 56 to operatively coupled the PED holder assembly 10H to the assistance request hub 54 and the power and/or data outlet 56. The hospital room configuration 40H can be implemented by adding the PED holder assembly 10H to an existing hospital room configuration that includes the bed 42 and the assistance request communication cable assembly 44H coupling the bed hub 92D to the assistance request hub 54. In the illustrated embodiment, the assistance request communication cable assembly 44H includes a single cable segment 130 that operatively connects the distal connector 82D to the proximal connector 72.

Figure 11:
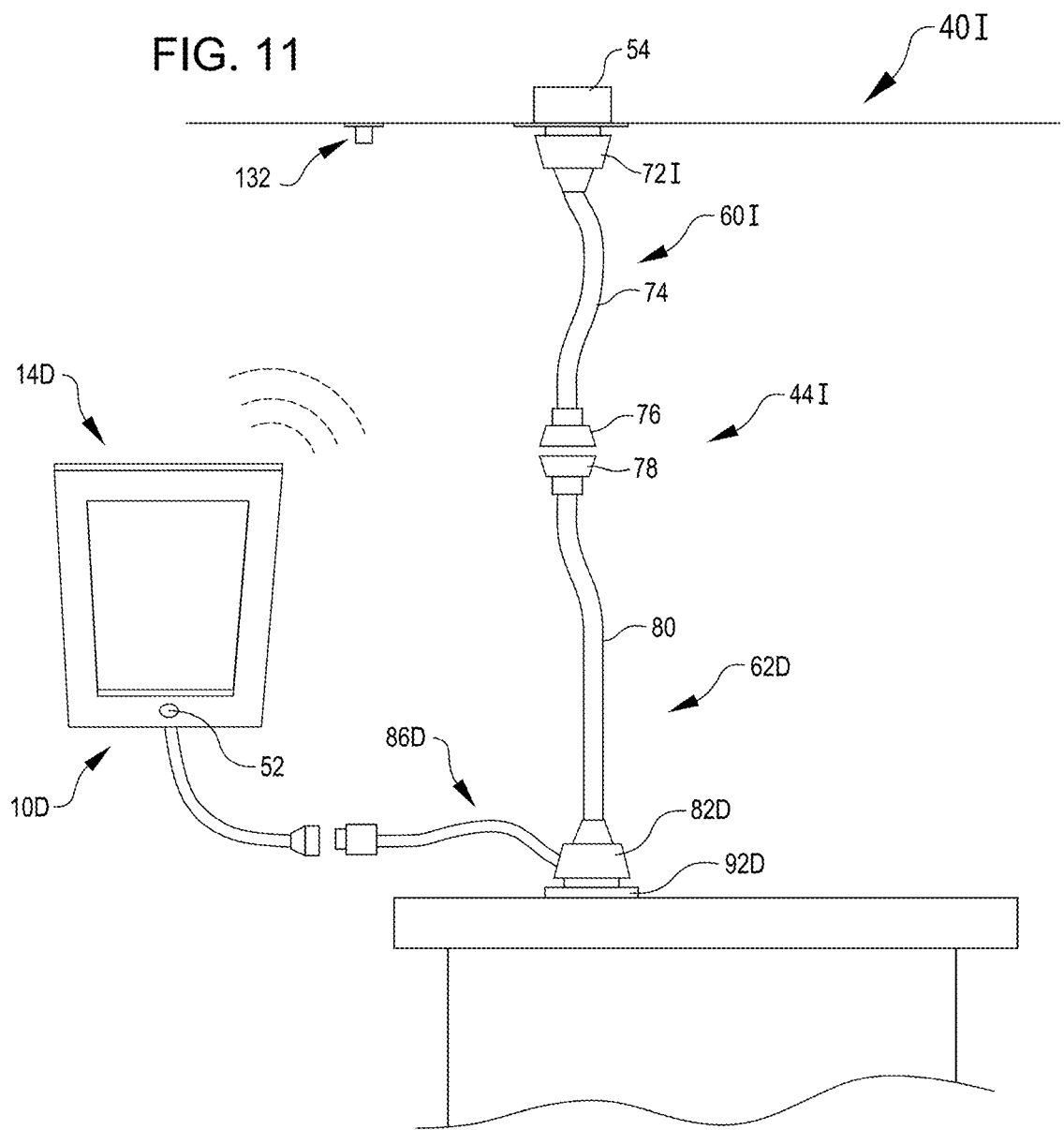
FIG. 11 shows a hospital room configuration in which a PED holder assembly is connected to a communication and power assembly for a patient bed, in accordance with embodiments, the PED holder assembly including a assistance request button and wireless communication functionality.

FIG. 11 shows a hospital room configuration 40i that is similar to the hospital room configuration 40E shown in FIG. 7 except for differences described below. The hospital room configuration 40i includes the PED holder assembly 10D and a assistance request communication cable assembly 44i. The assistance request communication cable assembly 44i is similar to the power and communication cable 44D shown in FIG. 6, but has a proximal cable assembly 60i that includes a proximal connector 72i that only connects to the assistance request hub 54 in contrast to the proximal connector 72 that connects to both the assistance request hub 54 and the power and/or data outlet 56 via the power and/or data cable assembly 58D as shown in FIG. 6. In the hospital room configuration 40i, the PED held by the PED holder 14D communicates wirelessly to a wireless router 132. The PED holder 14D can include a rechargeable battery that supplies power to recharge and/or operate the PED. In some embodiments, the PED holder assembly 10D supplies the PED with power transferred to the PED holder assembly 10D by the assistance request communication cable assembly 44i.

Figure 12:
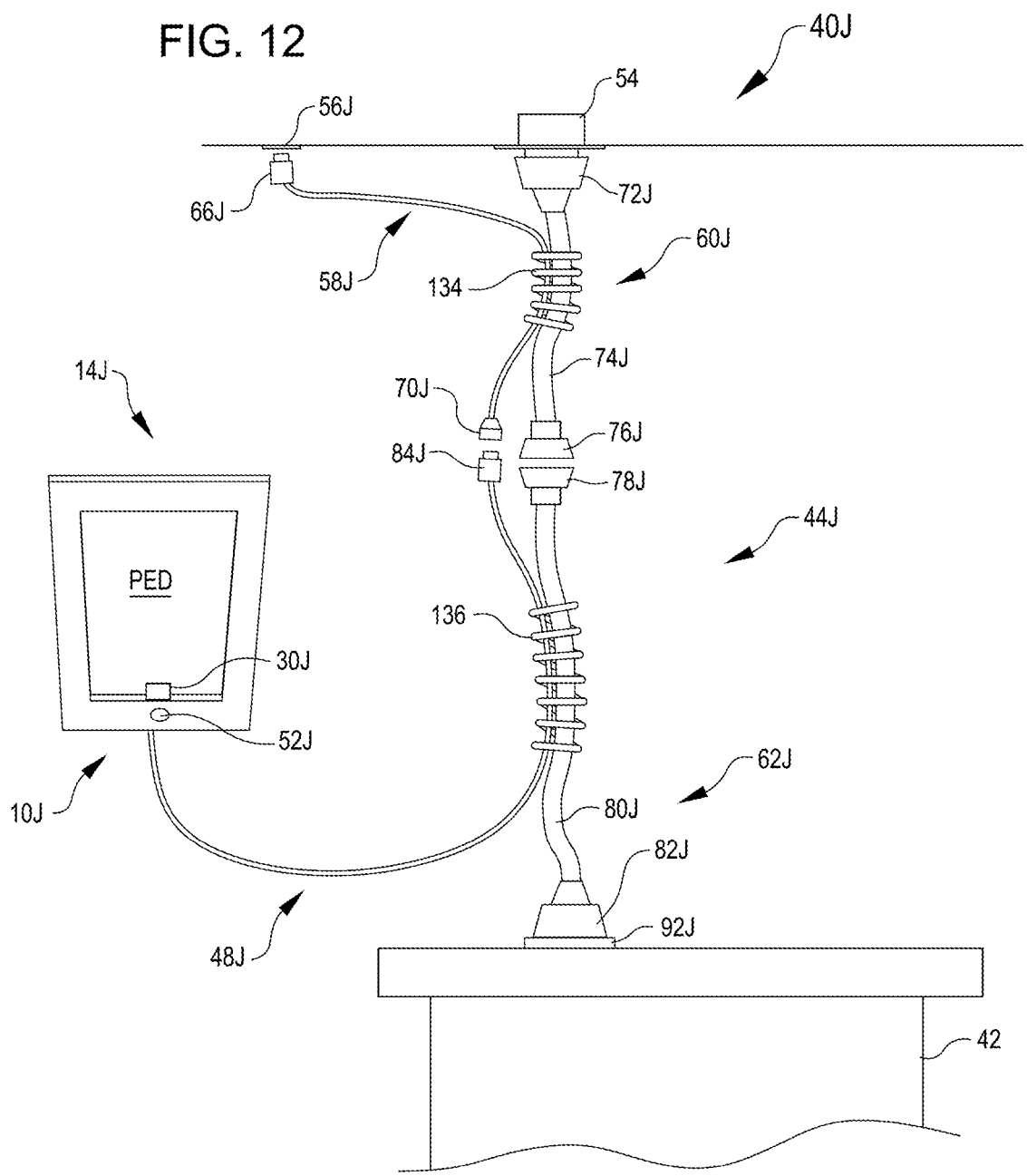
FIG. 12 shows a hospital room configuration that includes a PED holder assembly connected directly to a power and/or data device that supplies power and/or data to a PED, in accordance with embodiments, the PED holder assembly including a assistance request button and a connector disposed adjacent to a connector of a communication and power assembly for a patient bed.

FIG. 12 shows a hospital room configuration 40J that includes a PED holder assembly 10J, a power and data cable assembly 58J, a bed 42, and a assistance request communication cable assembly 44J. The PED holder assembly 10J includes a PED holder 14J and a power and data cable assembly 48J. The PED holder 14J includes a power and/or data output connector 30J for fitting into an input port 32 of a PED held by the PED holder 14J. The PED holder 14J further includes a assistance request button 52J that is operatively coupled to the connector 30J. The PED power and/or data cable assembly 58J includes a proximal connector 66J, a power and/or data cable 68J, and a distal connector 70J. The assistance request button 52J can be pressed to communicate a request for assistance to the PED held by the PED holder 30J. The power and data cable assembly 48J includes a proximal connector 84J that is connectable to the distal connector 70J to operatively connect the power and data cable assembly 48J to the outlet 56. The power and data cable assembly 48J operatively connects the power and/or data output connector 30 to a power and data outlet 56J via the power and data cable assembly 58J. In some embodiments, the PED held by the PED holder 14J, in response to receiving a request for assistance generated via pushing of the assistance request button 52J, transmits a request for assistance to an attendant station via the power and data outlet 56J. The assistance request communication cable assembly 44J includes a proximal cable assembly 60J and a distal cable assembly 62J. The proximal cable assembly 60J includes a proximal connector 72J, a communication cable 74J, and a distal connector 76J. The distal cable assembly 62J includes a proximal connector 78J, a communication cable 80J, and a distal connector 82J. The proximal connector 72J of the cable assembly 60J is connectable to the assistance request hub 54 to operatively connect the assistance request communication cable assembly 44J to the assistance request communication system. The proximal connector 78J of the cable assembly 62J is connectable to the distal connector 76J of the cable assembly 60J to operatively connect the cable assembly 62J to the assistance request communication system. The distal connector 82J of the cable assembly 62J is connectable to a bed connector 92J to operatively couple the bed 42 to the assistance request communication system.

In the illustrated embodiment, the distal cable assembly 62J is configured for quick disconnection from the proximal cable assembly 60J, and the power and data cable assembly 48J is configured for quick disconnection from the power and data cable assembly 58J, when the bed 42 needs to be moved. For example, the distal connector 76J and the proximal connector 78J can form a releasable magnetic connection, such as the magnetic connector disclosed in U.S. Pat. No. 9,147,965. As another example, the proximal connector 84J and the distal connector 70J can form a releasable magnetic connection, such as the magnetic connector disclosed in U.S. Pat. No. 9,147,965. In the illustrated embodiment, the proximal cable assembly 60J is coupled with the power and data cable assembly 58J via a proximal coupler 134, and the distal cable assembly 62J is coupled with the power and data cable assembly 48J via a distal coupler 136 so that the connectors 70J, 74J, 76J, 84J are held in close proximity to support quick disconnection of both connector 84J from connector 70J and connector 78J from connector 76J.

Figure 13:
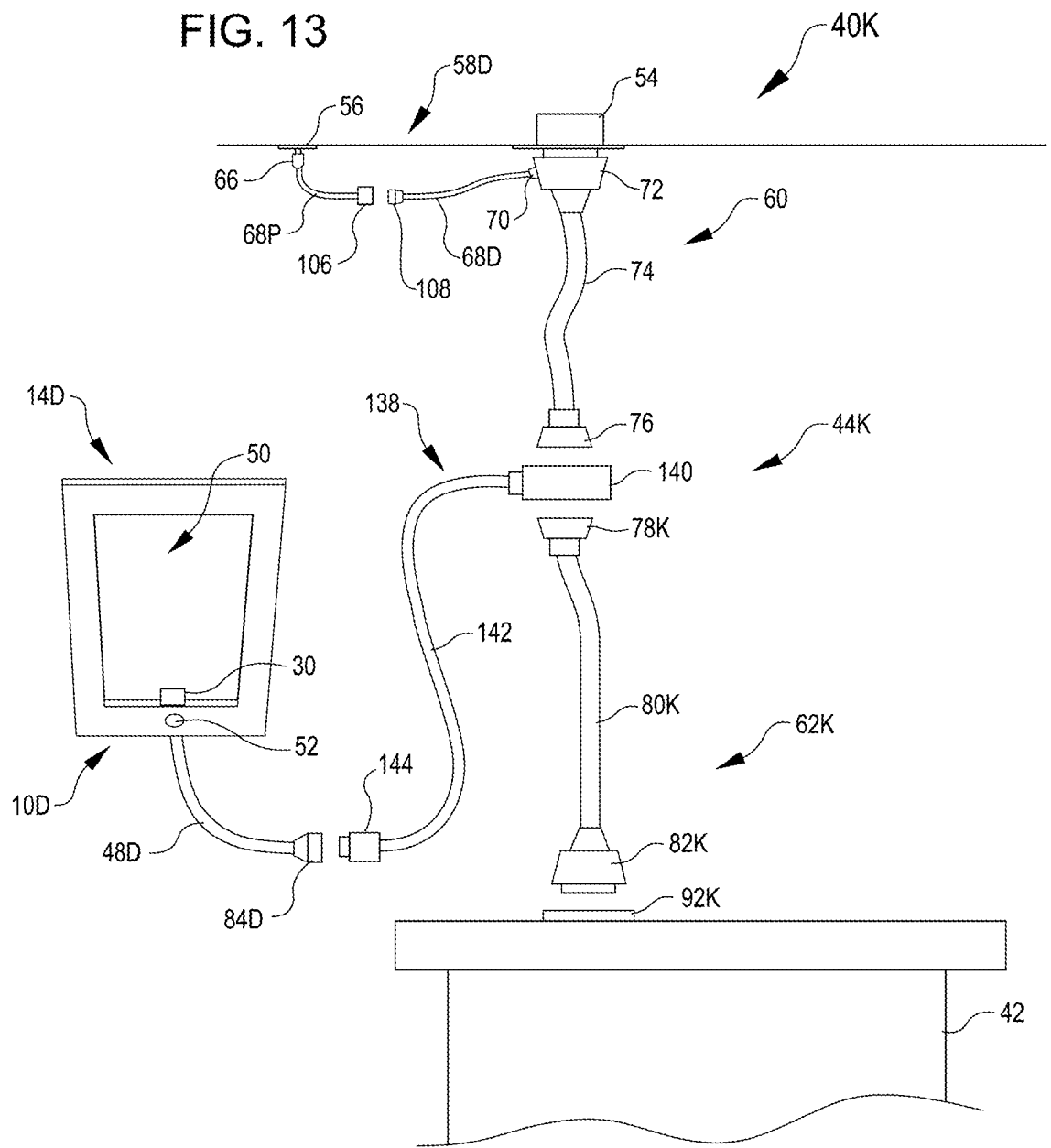
FIG. 13 shows a hospital room configuration in which a PED holder assembly is connected to a communication and power assembly for a patient bed, in accordance with embodiments, the PED holder assembly including a assistance request button.

FIG. 13 shows a hospital room configuration 40K that includes a hospital bed 42, a communication and power assembly 44K for the hospital bed 42, and the PED holder assembly 10D. The communication and power assembly 44K is configured similar to the communication and power assembly 44C, but including an intermediate coupler assembly 138. Reference identifiers associated with components of the communication and power assembly 44C that are the same or similar to components of the communication and power assembly 44K are the same or similar to reference identifiers associated with the components of the communication and power assembly 44K. The PED holder assembly 10D includes the proximal connector 84D, the cable assembly 48D, and the PED holder 14D. The PED holder 14D includes the power and/or data output connector 30 for fitting into an input port 32 of a PED held by the PED holder 14D. In the illustrated embodiment, the PED holder 14D includes a single assistance request button 52.

The communication and power assembly 44K operatively connects the PED holder assembly 10D to the assistance request communication system hub 54 and the outlet 56 and connects the bed 42 to the assistance request communication system hub 54 and, in some embodiments, the outlet 56. The power and/or data outlet 56 supplies power and/or data to a PED held by the PED holder 14D through the communication and power assembly 44K. The communication and power assembly 44K includes the PED power and/or data cable assembly 58D, the proximal cable assembly 60, and a distal cable assembly 62K. The distal cable assembly 62k includes a proximal connector 78K, a assistance request communication cable 80K, and a distal connector 82K. The PED power and/or data cable assembly 58D includes the proximal connector 66, a proximal cable 68P, a connector 106, a connector 108, a distal cable 68D, and the distal connector 70. The proximal connector 66 is connectable to the outlet 56; the connector 108 is connectable to the connector 106; and the distal connector 70 is connectable to the proximal connector 72 of the cable assembly 60 to operatively connect the communication and power assembly 44K to the power and/or data outlet 56. The proximal connector 72 of the cable assembly 60 is connectable to the hub 54 to operatively connect the communication and power assembly 44K to the assistance request communication system. The proximal connector 78K of the cable assembly 62K is indirectly connectable, via the intermediate coupler assembly 138, to the distal connector 76 of the cable assembly 60 to operatively connect the cable assembly 62K to the assistance request communication system and, in some embodiments, to the outlet 56. The bed 42 includes a bed hub 92K to which the distal connector 82K is connectable to operatively connect the bed hub 92K to the assistance request communication system and, in some embodiments, to the outlet 56. In some embodiments, the bed 42 includes any suitable number of assistance request buttons 52 that are operatively coupled with the assistance request communication system via the bed hub 92K.

The intermediate coupler assembly 138 operatively connects the PED holder assembly 10D to the communication and power assembly 44K. The intermediate coupler assembly 138 includes a coupler 140, a cable 142, and a distal connector 144 operatively connected to the cable 142. The cable 142 is operatively connected to the coupler 140 and extends from the connector coupler 140. The coupler 140 is connectable to and between the distal connector 76 and the proximal connector 78K to operatively couple the cable assembly 62K and the intermediate coupler assembly 138 to the cable assembly 60 and, thereby, to the assistance request communication system and the outlet 56. The proximal connector 84D is connectable to the distal connector 144 to operatively coupled the PED holder assembly 10D to the communication and power assembly 44K and, thereby, to the assistance request communication system and the power and/or data outlet 56.

The hospital room configuration 40K can include any suitable number of quick disconnection features that enhance the ability to move the bed 42 and/or the PED holder assembly 10D. For example, in some embodiments, the distal connector 76 and the coupler 140 form a quick release connection, such as the magnetic connector disclosed in U.S. Pat. No. 9,147,965. In some embodiments, the coupler 140 and the proximal connector 78K form a quick release connection, such as the magnetic connector disclosed in U.S. Pat. No. 9,147,965. In some embodiments, the distal connector 144 and the proximal connector 84D form a quick release connection, such as the magnetic connector disclosed in U.S. Pat. No. 9,147,965.

Figure 14:
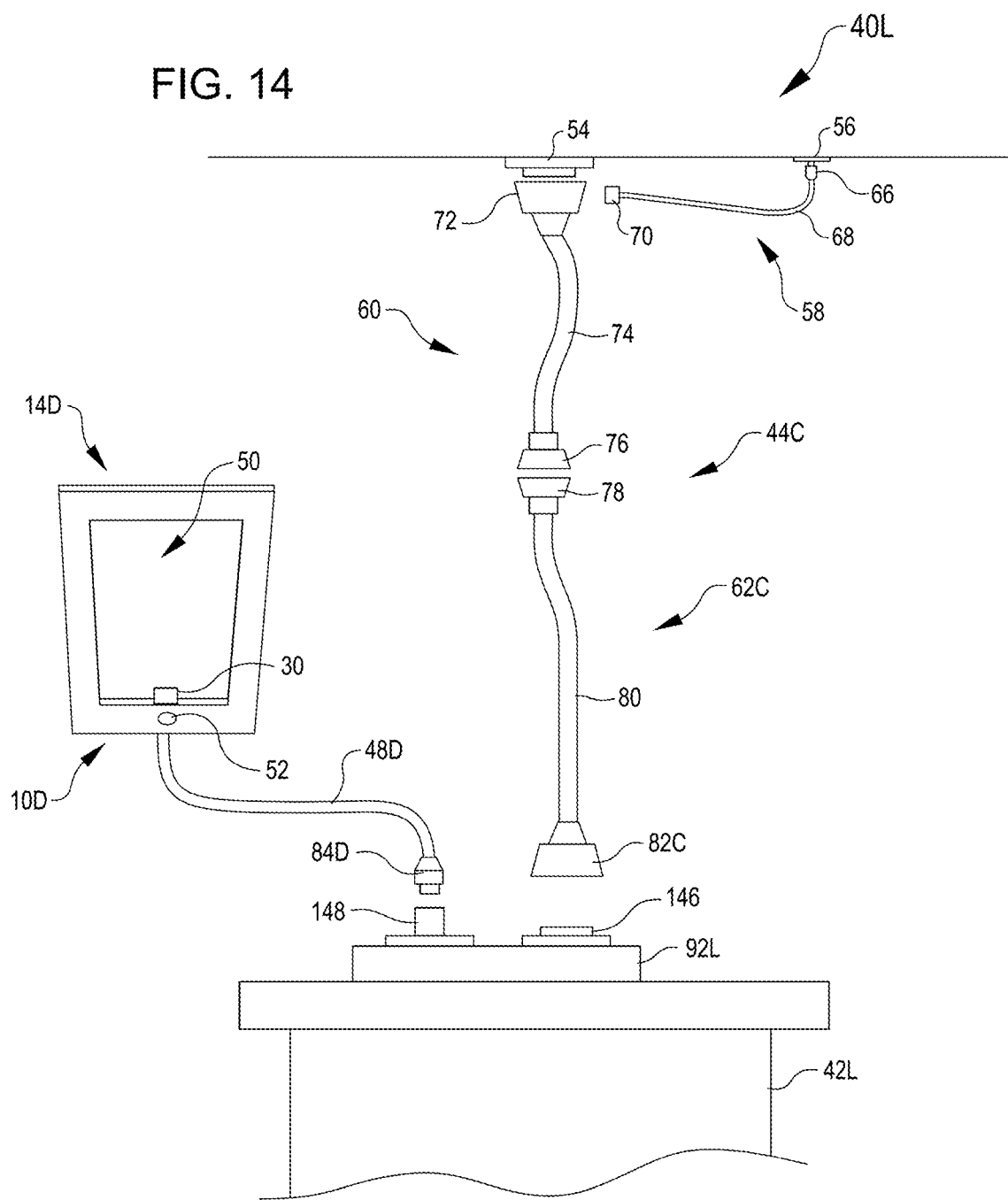
FIG. 14 shows a hospital room configuration in which a PED holder assembly is connected to a communication and power assembly for a patient bed, in accordance with embodiments, the PED holder assembly including a assistance request button.

FIG. 14 shows a hospital room configuration 40L that includes a hospital bed 42L, the communication and power assembly 44C, the PED holder assembly 10D. The bed 42L includes a bed hub 92L that includes a connector 146 and a connector 148. The distal connector 82C is connectable to the connector 146 to operatively connect the bed hub 92L to the assistance request communication system and the outlet 56. In some embodiments, the bed 42L includes any suitable number of assistance request buttons 52 that are operatively coupled with the assistance request communication system via the connector 146. The proximal connector 84D is connectable to the connector 148 to operatively connect the PED holder assembly 10D to the bed hub 92L and, thereby, to the assistance request communication system and the outlet 56 via the communication and power assembly 44C.

The hospital room configuration 40K can include any suitable number of quick disconnection features that enhance the ability to move the bed 42 and/or the PED holder assembly 10D. For example, in some embodiments, the distal connector 76 and the proximal connector 78 form a quick release connection, such as the magnetic connector disclosed in U.S. Pat. No. 9,147,965. In some embodiments, the distal connector 82C and the bed hub connector 146 form a quick release connection, such as the magnetic connector disclosed in U.S. Pat. No. 9,147,965. In some embodiments, the bed hub connector 148 and the proximal connector 84D form a quick release connection, such as the magnetic connector disclosed in U.S. Pat. No. 9,147,965.

Figure 15:
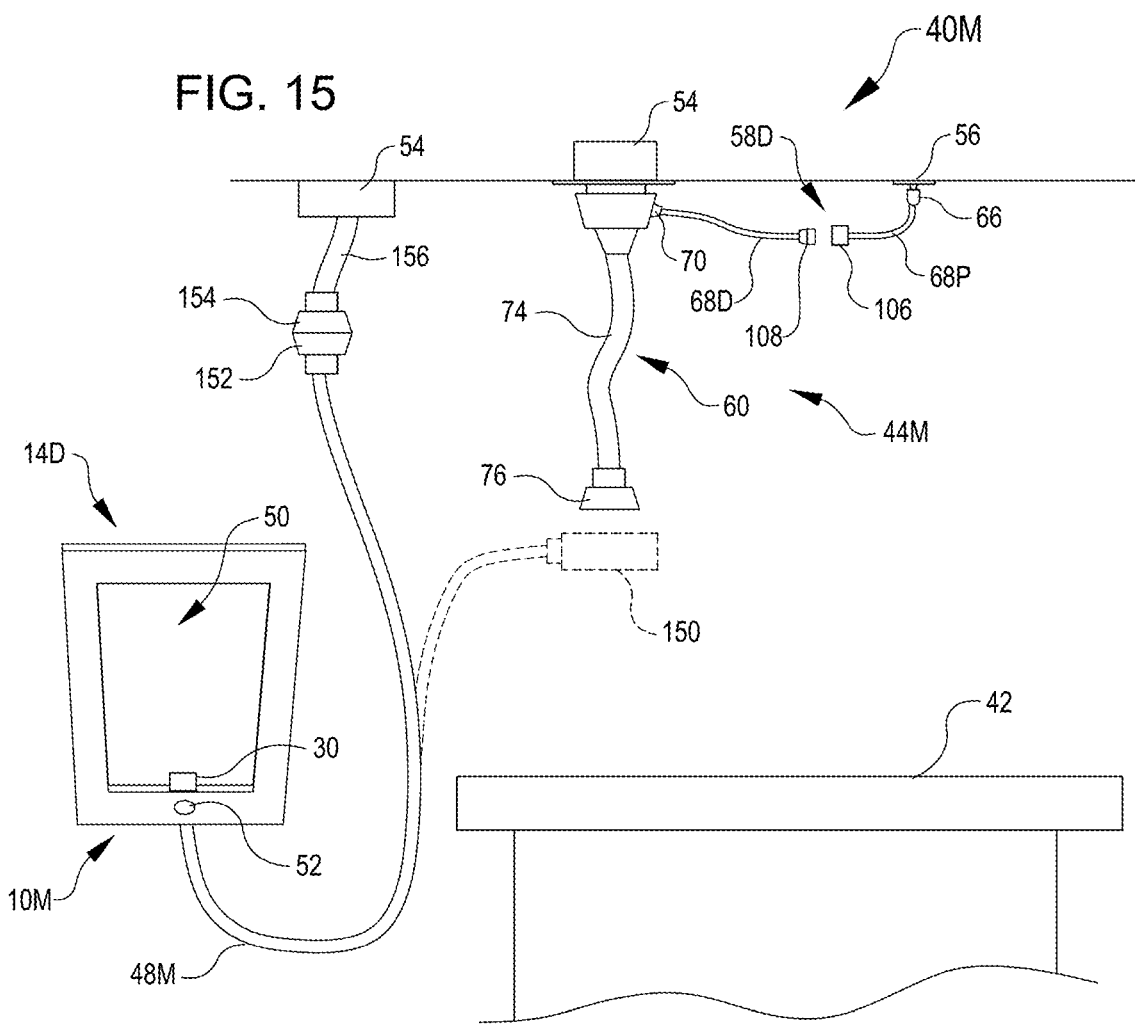
FIG. 15 shows a hospital room configuration that includes a PED holder assembly that can be connected to a communication and power assembly for a patient bed or connected directly to a power and/or data device that supplies power and/or data to a PED, in accordance with embodiments, the PED holder assembly including a assistance request button.

FIG. 15 shows a hospital room configuration 40M that includes a hospital bed 42, a communication and power assembly 44M, and a PED holder assembly 10M. The communication and power assembly 44M includes the PED power and/or data cable assembly 58D and the proximal cable assembly 60. The PED holder assembly 10M is configured similar to the PED holder assembly 10D. The PED holder assembly 10M includes the PED holder 14D, a power and communication cable 48M, and a proximal connector. In some embodiments, the proximal connector of the PED holder assembly 10M is a proximal coupler 150. The proximal coupler 150 is connectable to the distal connector 76 to operatively couple the PED holder 14D to the assistance request hub 54 and the power and/or data outlet 56 via the power and communication cable 48M. In some embodiments, the proximal connector of the PED holder assembly 10M is a proximal connector 152. The proximal connector 152 is connectable to a distal connector 154 to operatively couple the assistance request button 52 of the PED holder assembly 10M to a assistance request hub 54 via a connection cable 156. In some embodiments, the assistance request hub 54 supplies power to the PED holder 14D via a power transmission path including the connection cable 156, the distal connector 154, the proximal connector 152, the power and communication cable 48M, and the power and/or data output connector 30.

The hospital room configuration 40M can include any suitable number of quick connection features for operatively coupling the PED holder assembly 10M to a assistance request hub 54 or to both a assistance request hub 54 and a power and/or data outlet 56. For example, in some embodiments, the distal connector 76 and the proximal coupler 150 form a quick release connection, such as the magnetic connector disclosed in U.S. Pat. No. 9,147,965. In some embodiments, the distal connector 154 and the proximal connector 152 form a quick release connection, such as the magnetic connector disclosed in U.S. Pat. No. 9,147,965.

Figure 16:
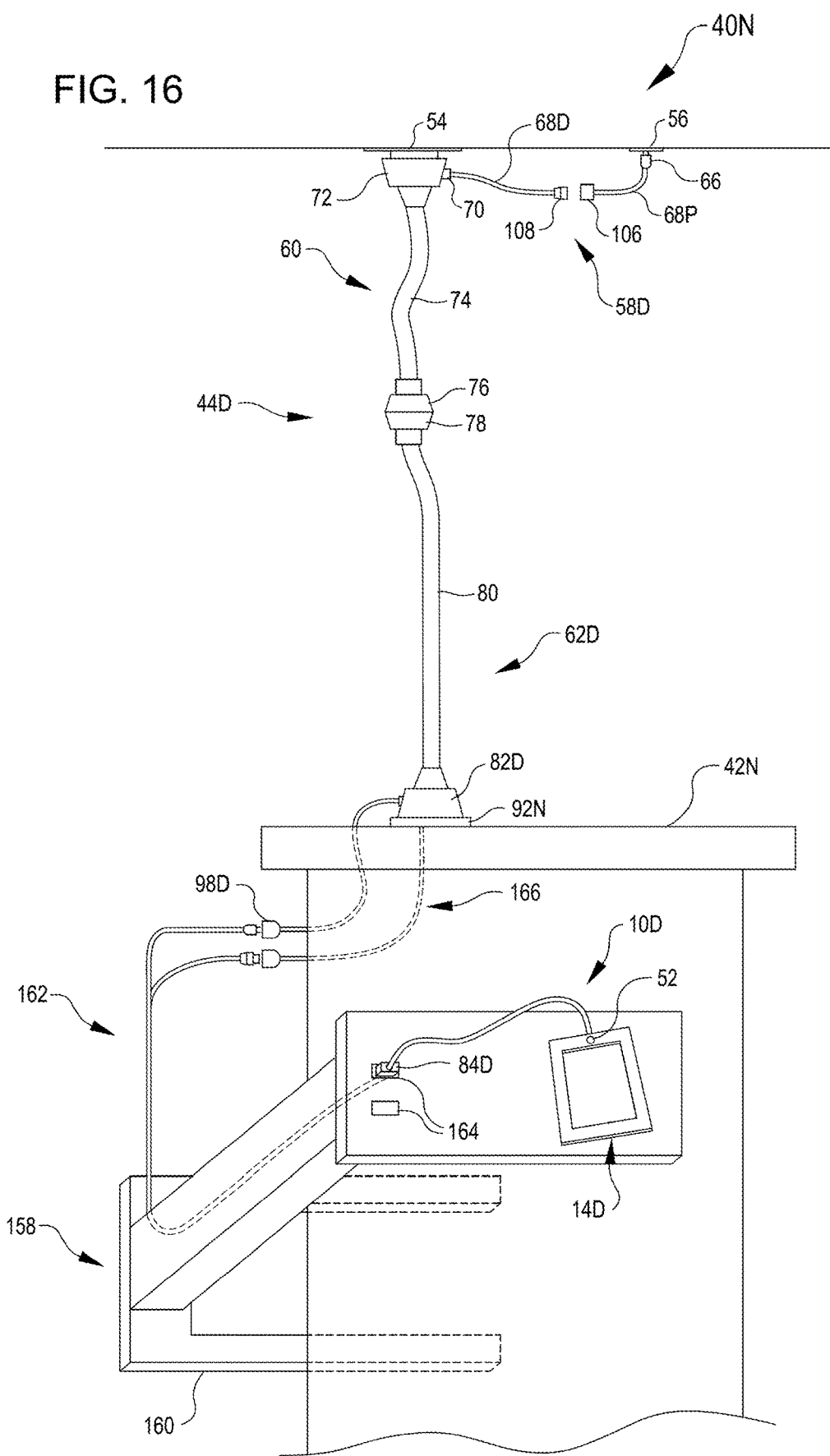
FIG. 16 shows a hospital room configuration in which a PED holder assembly is connected to a bed stand assembly connected to a communication and power assembly for a patient bed, in accordance with embodiments, the PED holder assembly including a assistance request button.

FIG. 16 shows a hospital room configuration 40M that includes a hospital bed 42N, the communication and power assembly 44D, the PED holder assembly 10D, and a bed stand assembly 158. The communication and power assembly 44D includes the PED power and/or data cable assembly 58D, the proximal cable assembly 60, and the distal cable assembly 62D. The bed 42N includes a bed hub 92N to which the distal connector 82D can be coupled to operatively couple the bed hub 92N to the assistance request hub 54 and the power and/or data outlet 56 via the communication and power assembly 44D.

The bed stand assembly 158 includes a bed stand 160, a connection cable assembly 162, and connection ports 164 mounted to the bed stand 160. The connection cable assembly 162 operatively couples each of the connection ports to both the bed hub 92N and the distal cable assembly 62D. In the illustrated embodiment, the connection cable assembly 162 is connectable to the bed hub 92N via a connection cable 166 to operatively couple each of the connection ports 164 to the assistance request hub 54 via the communication and power assembly 44D. Also in the illustrated embodiment, the connection cable assembly 162 is connectable to the distal connector 98D of the distal cable assembly 62D to operatively couple each of the connection ports 164 to the power and/or data outlet 56 via the communication and power assembly 44D. The proximal connector 84D of the PED holder assembly 10D is connectable to any one of the connection ports 164 to operatively couple the PED holder 14D to the assistance request hub 54 and the power and/or data outlet 56.

The hospital room configuration 40N can include any suitable number of quick disconnection features that enhance the ability to move the bed 42 and/or the bed stand assembly 158. For example, in some embodiments, the distal connector 76 and the proximal connector 78 form a quick release connection, such as the magnetic connector disclosed in U.S. Pat. No. 9,147,965.

Figure 17:
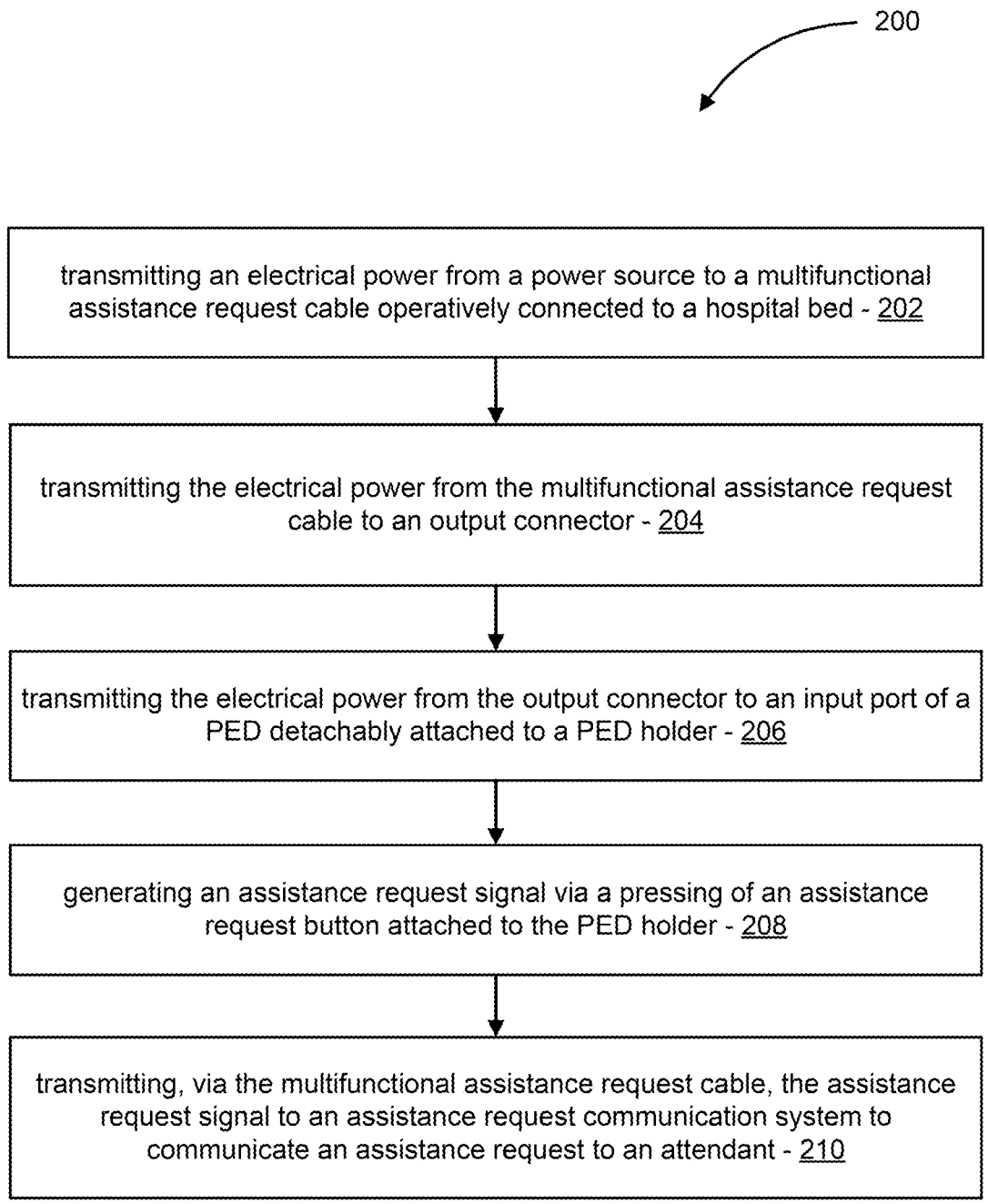
FIG. 17 is a simplified schematic diagram of a method of transmitting power to a portable electronic device (PED) over a multifunctional assistance request cable and a request for assistance signal over the multifunctional assistance request cable, in accordance with embodiments.

FIG. 17 is a simplified schematic diagram of a method 200 of transmitting power to a portable electronic device (PED) over a multifunctional assistance request cable and a request for assistance signal over the multifunctional assistance request cable, in accordance with embodiments. Any suitable assemblies, such as assemblies described herein, can be used to practice the method 200. The method 200 includes transmitting an electrical power from a power source to a multifunctional assistance request cable operatively connected to a hospital bed (act 202), transmitting the electrical power from the multifunctional assistance request cable to an output connector (act 204), transmitting the electrical power from the output connector to an input port of a PED detachably attached to a PED holder (act 206), generating an assistance request signal via a pressing of an assistance request button attached to the PED holder assembly (act 208), and transmitting, via the multifunctional assistance request cable, the assistance request signal to an assistance request communication system to communicate an assistance request to an attendant (act 210). Acts 202-210 can be accomplished using any suitable approach, such as the approaches described herein.

FIGS. 18-21 show a surface-mounted electronic device holder positioned on a surface, such as on a wall outside a room of a health care facility. The surface-mounted electronic device holder may include information such as an identifier of the room as well as information related to the health care facility. In some examples, the surface-mounted electronic device holder may be positioned within the room, or may be positioned away from the room, such as at a standalone station where personnel may interact with the electronic device, such as to update health records of patients within the facility. The electronic device contained within the holder may be a self-contained electronic device, such as a personal electronic device (PED), or may be a built-in electronic device. The electronic device may be connected to a wired or wireless network of the health care facility and may also be connected to one or more other electronic devices through a wireless or wired connection, such as through an ethernet cable which may provide both power and data connections to the electronic device, for example through a power-over-ethernet (POE) connections. The surface-mounted electronic device holder may also include additional means of displaying information, such as with moveable flags to attract attention, projected displays, illuminated lights, sound-producing devices, and other such output devices. The holders include room identifying information as well as the electronic device displaying information about the room, patient, or other such information. The holder may also include input and output devices as described above. The holder may also include connections for data and power connection of the electronic device to a system of the health care facility. The holder may also include proximity sensors, RFID sensors, and other such sensors for detecting a presence of and verifying an identity of an individual who approaches the room.

In some examples, the surface-mounted electronic device holder may provide a voice and/or a video communication interface into a room of the healthcare facility, for example for a physician to check on the status of a patient before entering a room. The device holder may include input devices, such as a physical button to interact with the electronic device, a microphone, touch screen, and other such input devices for interacting with the electronic device in various ways.

Figure 18:
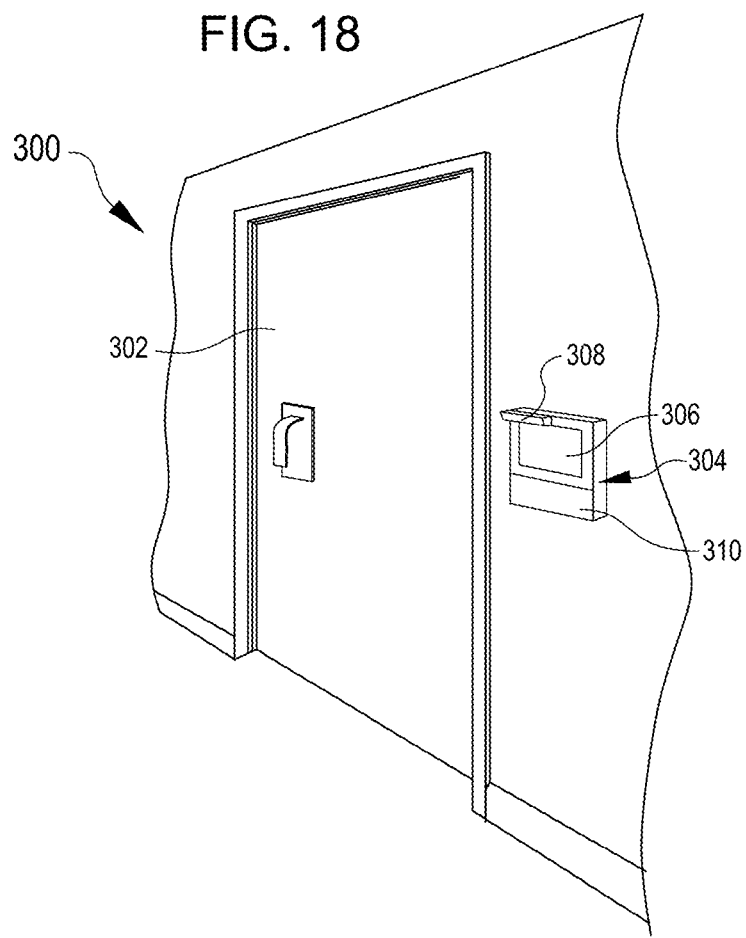
FIG. 18 shows a doorway in a hospital facility with a PED holder assembly positioned on the wall to present information and receive inputs, in accordance with some embodiments.

As illustrated in FIG. 18, the entrance to a patient room 300 a surface-mounted electronic device holder 304 is shown positioned on a wall of a health care facility adjacent a door 302. The surface-mounted electronic device holder 304 may include a display 306, which may a display of a PED as described herein. The surface-mounted electronic device holder 304 may also include physical identification information, such as a marking indicating a room such as a room number in alphanumeric characters and/or other characters such as braille or other fixed features on a housing 310. The housing may include devices 308 for attaching or affixing temporary placards, papers, notes, and other such materials that may be placed or referenced by staff within the healthcare facility. The housing 310 may include a surface on which notes may be written directly, such as a surface that is non-permeable and smooth capable of writing on with dry-erase markers, whiteboard markers, and the like.

Figure 19:
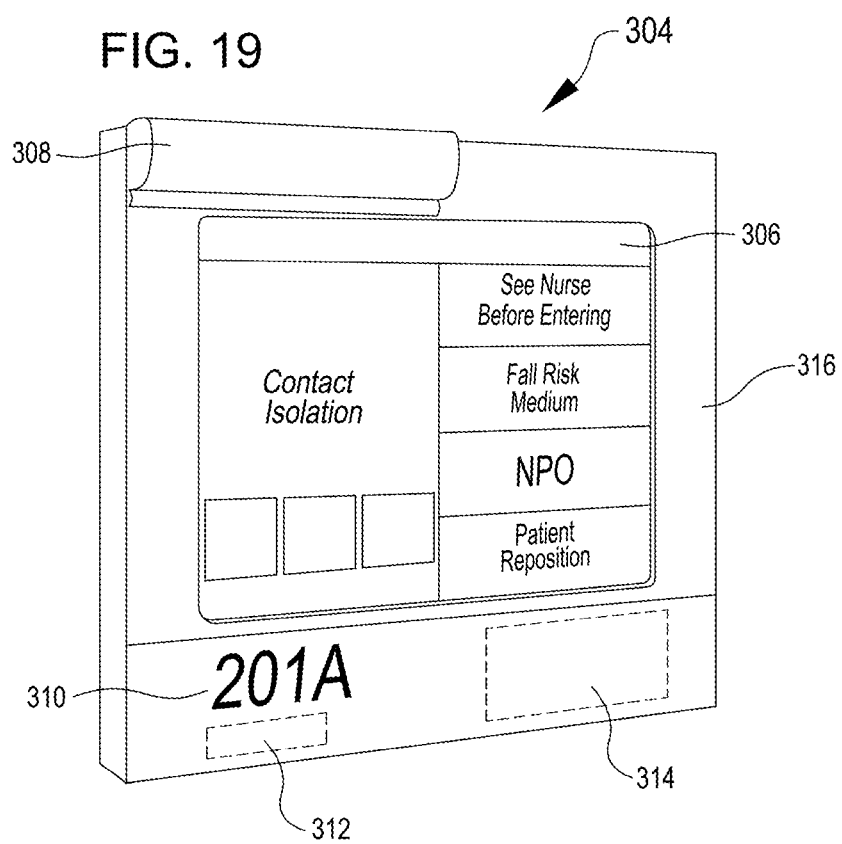
FIG. 19 shows a wall-mounted PED holder assembly including a display of the PED and device for receiving input data, in accordance with some embodiments.

Turning now to FIG. 19 a surface-mounted electronic device holder 304 (hereafter "holder 304") is shown with enclosing an electronic device including a display 306. The housing 316 defines an opening around the display 306 where the display 306 is visible and a user may interact with the display 306. The holder 304 may also include additional means of displaying information, such as with moveable flags to attract attention, projected displays, illuminated lights, sound-producing devices, and other such output devices. The holder 304 includes room identifying information 310 as well as the electronic device displaying information about the room, patient, or other such information. The holder 304 may also include input and output devices as described above. The holder 304 may also include connections for data and power connection of the electronic device to a system of the health care facility. The holder may also include proximity sensors 312, and authentication devices 314 which may include RFID sensors, and other such sensors for detecting a presence of and receiving authentication information for verifying an identity of an individual who approaches the room. Additional features of the holder 304 may include physical buttons for interacting with the electronic device, vent holes, securing features such as security screws, sliding locks, magnetic locks, and the like to prevent removal of the electronic device, except by authorized personnel.

In some examples, the holder 304 may be releasably secured to the wall, or other surface, through the use of a releasable securement or locking device. The releasable securement may include a slider, hook, magnetic latch, or other such releasable attachment mechanism. The releasable securement may enable the holder 304 to be carried into a patient room or within some limited predetermined range, such as set by beacons, geofences, or other such limitations. Upon passing or reaching such geographic limitations a signal may be conveyed to generate a notification that the holder 304 has been removed to a system of a healthcare facility. Additionally warning signals and/or tracking information may be included to aid in recovery of the device if removed.

In some examples, the holder 304 may be released, such that the holder 304 is removable from the wall, or other surface, after an identity of a user has been authenticated, for example using the authentication device 314 described herein. For example, a caregiver may approach the holder 304, adjacent a patient room, and may authenticate their identity with appropriate credentials, upon authentication of credentials the releasable securement may enable removal of the holder 304, or a portion of the holder 304 from the wall such that the caregiver can carry the holder 304 with the electronic device into the patient room for use in taking notes or otherwise facilitating caregiving tasks. The releasable securement may receive a signal from the electronic device, or a controller device, in response to verification of the authentication credentials, the signal releasing a mechanical, electrical, magnetic, or other actuatable locking mechanism such that the holder 304 may be removed. Before authentication of the caregiver, the holder 304 may be locked in place and not removable.

The display 306 may include information related to care of the individual in the room, reservation, order, or other such information, and may include information gathered from within the room, including information relating to a position of the bed, an alert light signaled by an alert switch, or other such information.

Figure 20:
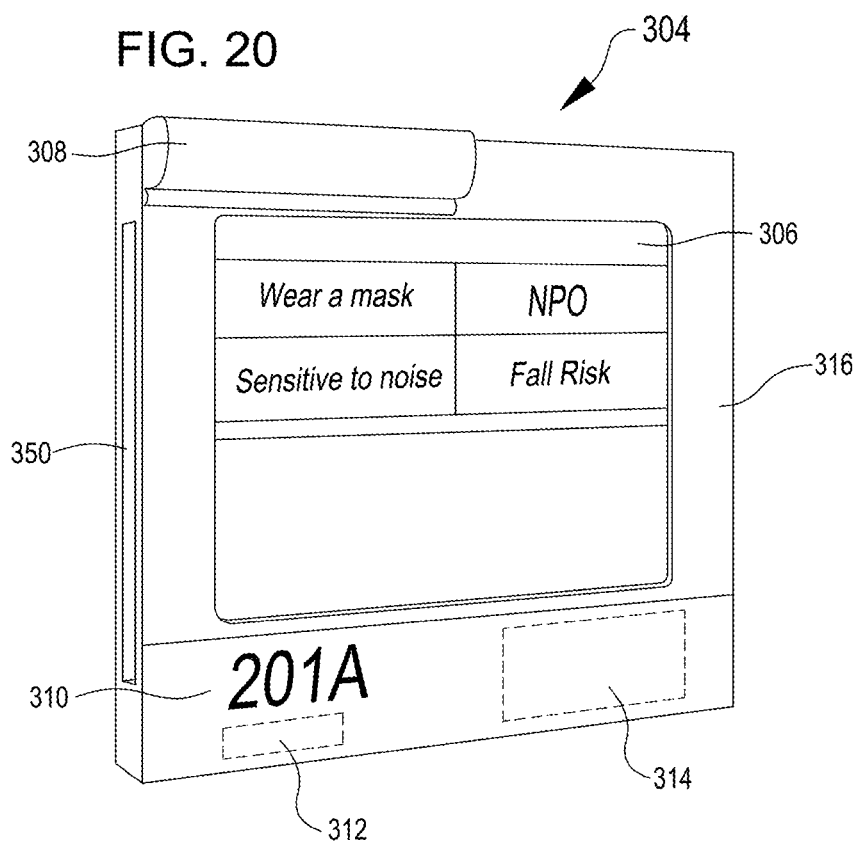
FIG. 20 shows a wall-mounted PED holder assembly including configurable illumination devices around the perimeter of the assembly, in accordance with some embodiments.

Turning now to FIG. 20, the holder 304 is shown including configurable light emitting devices 350 around the perimeter of the housing 316. The light emitting devices 350 may provide a visual indication of a room status, for example with green lights or dim lights indicating a normal condition while flashing lights or red lights may indicate an emergency status within the room. The light emitting devices 350 may also indicate, for example that the patient is resting, reclined, out of the room, or any other patient status. In some examples, the light emitting devices 350 may be accompanied by or replaced with one or more projection devices to project displays onto a floor, ceiling, or wall of the health care facility. The projection may indicate, for example a stop sign to indicate that a room should not be entered, or to project some particular information relating to a patient. The light emitting devices 350 may be configured based upon a signal from the electronic device or based on a signal from a central system of the health care facility.

In some examples, the surface-mounted electronic device holder 304 may be accompanied by one or more peripheral devices, such as a hand sanitizing station. The electronic device may be linked to the station such that confirmation of personnel sanitizing hands can be accomplished. This may include a proximity sensor, camera, contact sensor, or other such means of confirming use of the hand sanitizing station. In some examples, the person may approach a room and the illumination panels may illuminate in a first color, red. The electronic device may display a message instructing the person to sanitize their hands. Following confirmation of hand sanitizing, the lights may change to green, indicating the person may enter the room.

In some examples, the surface-mounted electronic device holder 304 may include sensors to receive identifying information, such as RFID sensors acting as authentication sensors 314. The electronic device, or a system of the health care facility, may verify the identity of the person and perform an action. For example, the lights of the holder may indicate that a person should not enter a room, or that a room is secured. Following verification of the identity of the person, the lights may change color to indicate the person may enter the room. In some examples a lock or other such system may also be controlled such that only authorized persons can enter a room of the health care facility. In some examples, the electronic device may display a first set of information and subsequently, after verification of an identity of an individual, may display a second set of information as described with respect to FIG. 23. For example, the display may initially present general information and, upon verification of the identity of a health care professional, may display patient information to the professional for their use. Such personal information is thereby protected for the patient and easily accessible to the professional. In some examples, the surface-mounted electronic device holder may include one or more interfaces for communicating with other electronic devices, such as through BLUETOOTH®. The other electronic devices may include electronic devices of personnel associated with the health care facility, for example to update patient records from a physician device.

Figure 21:
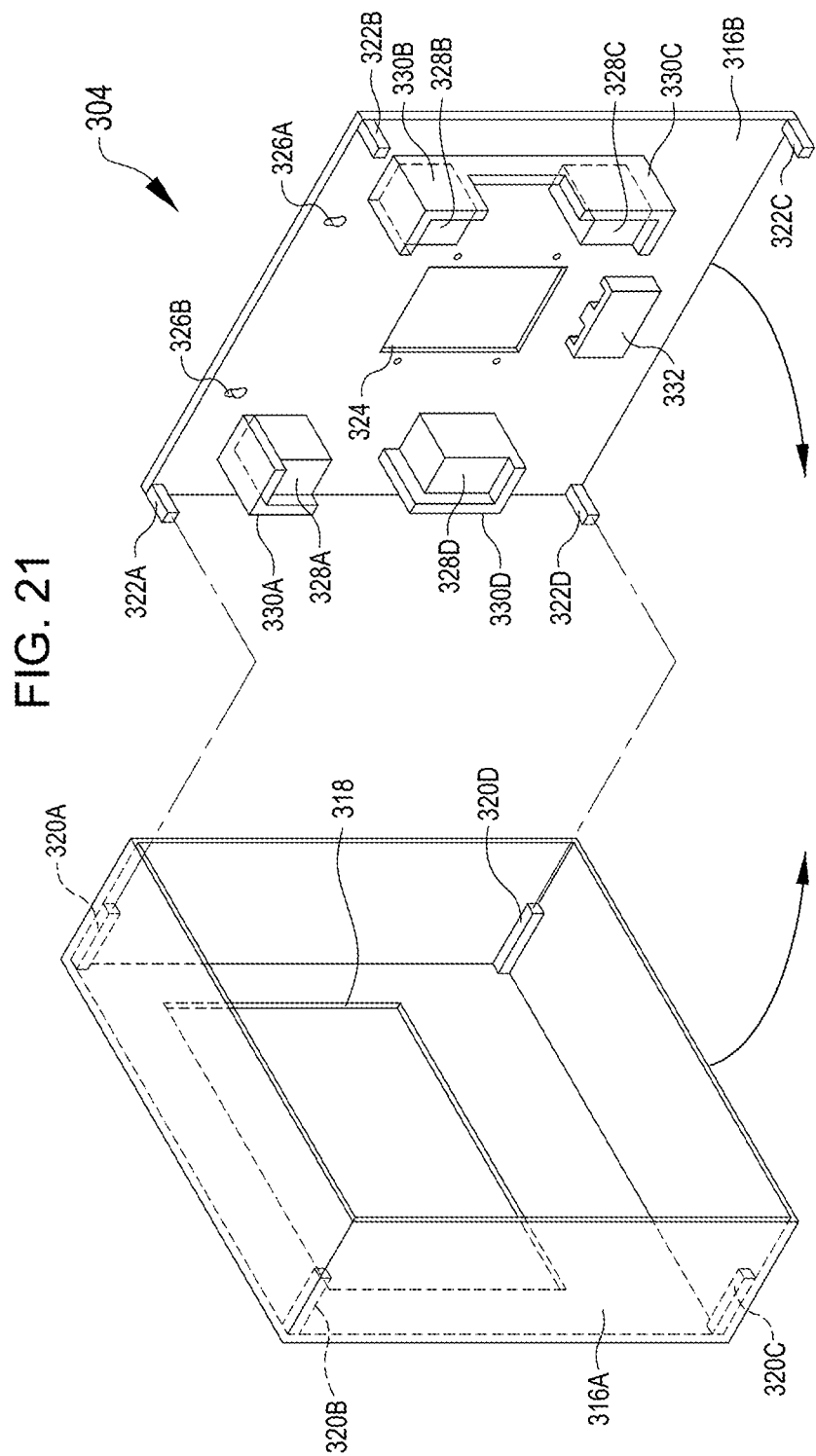
FIG. 21 shows the wall-mounted PED holder assembly in an open configuration, in accordance with some embodiments.

Turning now to FIG. 21, the surface-mounted electronic device holder 304 is shown in an open configuration, in accordance with some embodiments. As illustrated, the holder 304 may be formed of two or more components, such as a front 316A and a back 316B. In some examples, the holder 304 may be a unibody assembly with an opening to insert or access an electronic device contained therein. The front 316A defines an opening 318 through which a display of the electronic device may be visible and/or interacted with. For example, the display may include a touchscreen that can be interacted with by a user through opening 318.

The front 316A includes walls and also includes internal components 320 for interfacing with components of back 316B to positively engage when assembled together. The internal components 320 are shown as blocks that rest in the corners of the front 316A such that when front 316A and back 316B are assembled together internal components 322 on the back 316B engage with the corners of the front 316A as well as the internal components 320 so positively engage and secure the front 316A and back 316B together in a single location and orientation. Additional features, including security screws, magnets, cam-locks, pins, or any other such fasteners may be used to secure the front 316A and the back 316B together.

The back 316B defines an opening 324 where one or more connections or interfaces 332 may be inserted to connect an electronic device within the holder 304 to other systems, such as systems and networks of a hospital, including power and data connections, such as a POE connection as described herein. The POE connection may provide a power and data connection to enable the exchange of information as well as power to the electronic device without the need for more than a single interface or cable. In some examples, the holder 304 may also enclose a backup power supply, such as a battery backup that enables the electronic device or peripherals attached thereto (cameras, lights, sensors) to continue to function independent of a wired power connection. Connections to power and data, such as through POE connections are included within the holder and provide a conduit for communication between the electronic device and a system of the health care facility.

The electronic device within the holder 304 may communicate with other devices, such as other hospital equipment, for example to display information related to a status of various devices and/or equipment in a patient room. The electronic device may be entirely standalone, not requiring computing power or resources of a remote computing device or server. In some examples, the electronic device may communicate with one or more elements within the holder 304, or within an environment entirely over BLUETOOTH®.

The back 316B includes cradling features 330 to support an electronic device or a display of an electronic device to maintain the electronic device such that the display is aligned with the opening 318. The cradling features 330 include rear surfaces 328 to support a back of the electronic device and also include raised edges to resist and/or prevent lateral and/or vertical movement of the electronic device. Though illustrated with four cradling features 330, in some embodiments more or less cradling features 330 may be included to support the electronic device in the holder 304.

Figure 22:
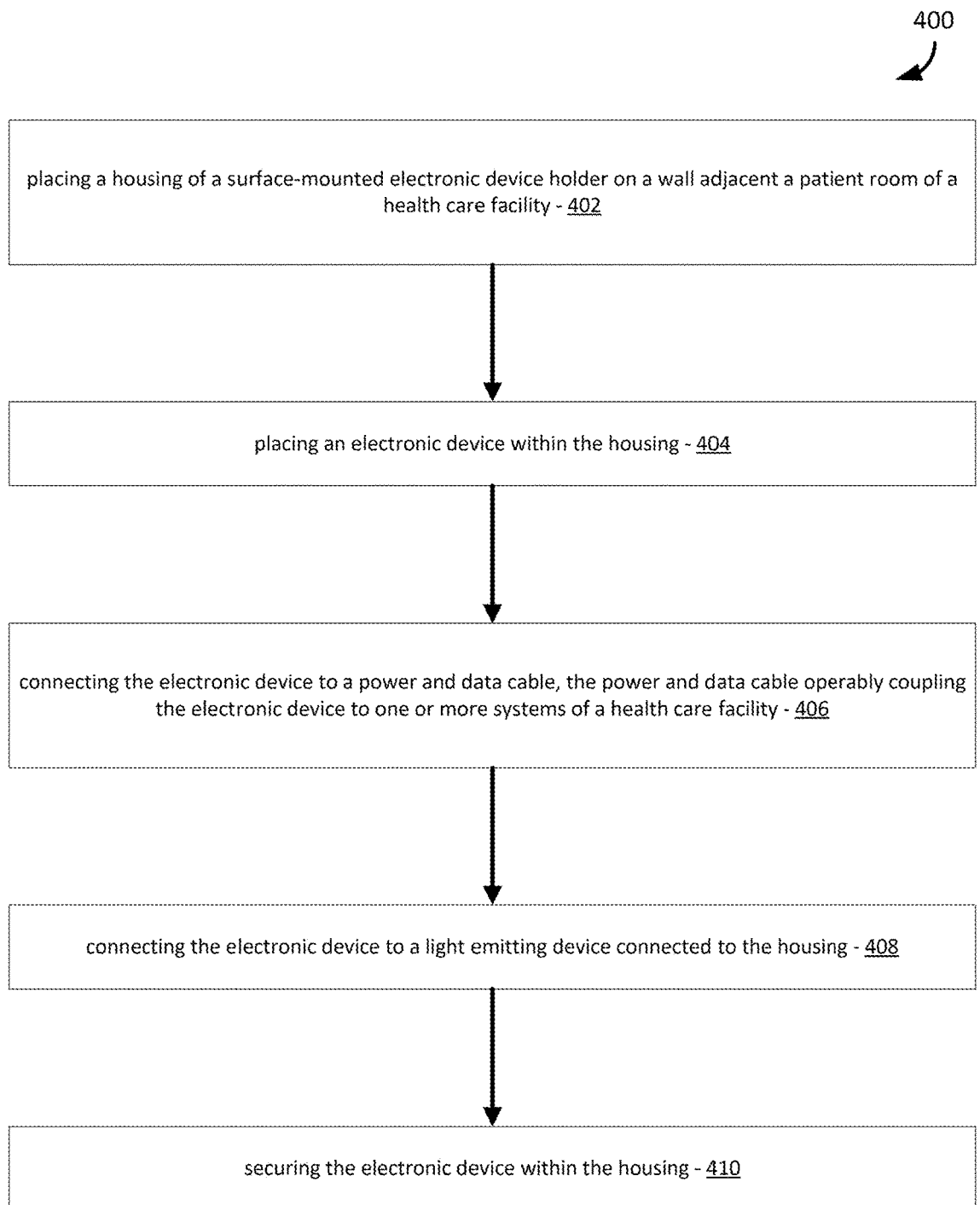
FIG. 22 is a simplified schematic diagram of a method of installing the wall-mounted PED holder assembly, in accordance with some embodiments.

FIG. 22 is a simplified schematic diagram of a method 400 of installing the wall-mounted PED holder assembly, in accordance with some embodiments. The wall-mounted PED holder assembly may be the surface-mounted PED holder 304 in some examples. In some examples, the holder may be installed on a wall or surface of a hospital or health care facility, for example adjacent an entry to patient room, in a hallway, within a patient room, adjacent a chair or bed, adjacent an exam table, or in any other suitable location.

At 402, the method 400 includes placing a housing of a surface-mounted electronic device holder on a wall adjacent a patient room of a health care facility. The housing may include a mounting plate, such as back 316B of FIG. 21. The back 316B may be secured to the wall using any suitable attachment means for securing to a wall or surface in a permanent or non-permanent manner.

At 404, the method 400 includes placing an electronic device within the housing. The electronic device may be a self-contained device such as a computer or tablet or may be a series of components connected or operably coupled together, such as a processor, memory, display device, and other such components. The electronic device may be placed within the housing such that the display is visible through an opening in the housing. The electronic device may be supported by supports to resist movement of the electronic device within the housing once installed.

At 406, the method 400 includes connecting the electronic device to a power and data cable, the power and data cable operably coupling the electronic device to one or more systems of a health care facility. The power and data cable may be connected to an interface as described herein, including a POE connection or other such connection to provide power and/or data connection to the electronic device.

At 408, the method 400 includes connecting the electronic device to a light emitting device connected to the housing. The electronic device may power the light emitting device or the light emitting device may include a separate power source. The light emitting device may include color-configurable light elements, projectors, such as to project an image, incandescent lights, LEDs, fluorescent lights, and the like. The electronic device may also be connected to other devices including, for example a handwashing station, a flag or visual marker, or any other suitable device that may be connected to the electronic device. Additional devices may include communication devices, proximity sensors, authentication devices, RFID sensors, biometric devices, wireless communication devices, and the like. In some examples, the flag or other such movable features may be actuated in response to a signal from the electronic device or a health care system. The flag or other such movable feature may be connected to a motor, such as a stepper motor, and the signal may cause the motor or any other suitable actuator to change a position of the flag, for example to draw attention to a room, indicate occupancy of a room, or provide other such signals as visual cues.

At 410, the method 400 includes securing the electronic device within the housing. The housing may be closed around the electronic device by securing portions of the housing together to enclose the electronic device. In some examples the housing may include a removable access panel that may be secured. The electronic device may be secured with security devices such as security screws, magnetic latches, sliding locks, and other such devices.

Figure 23:
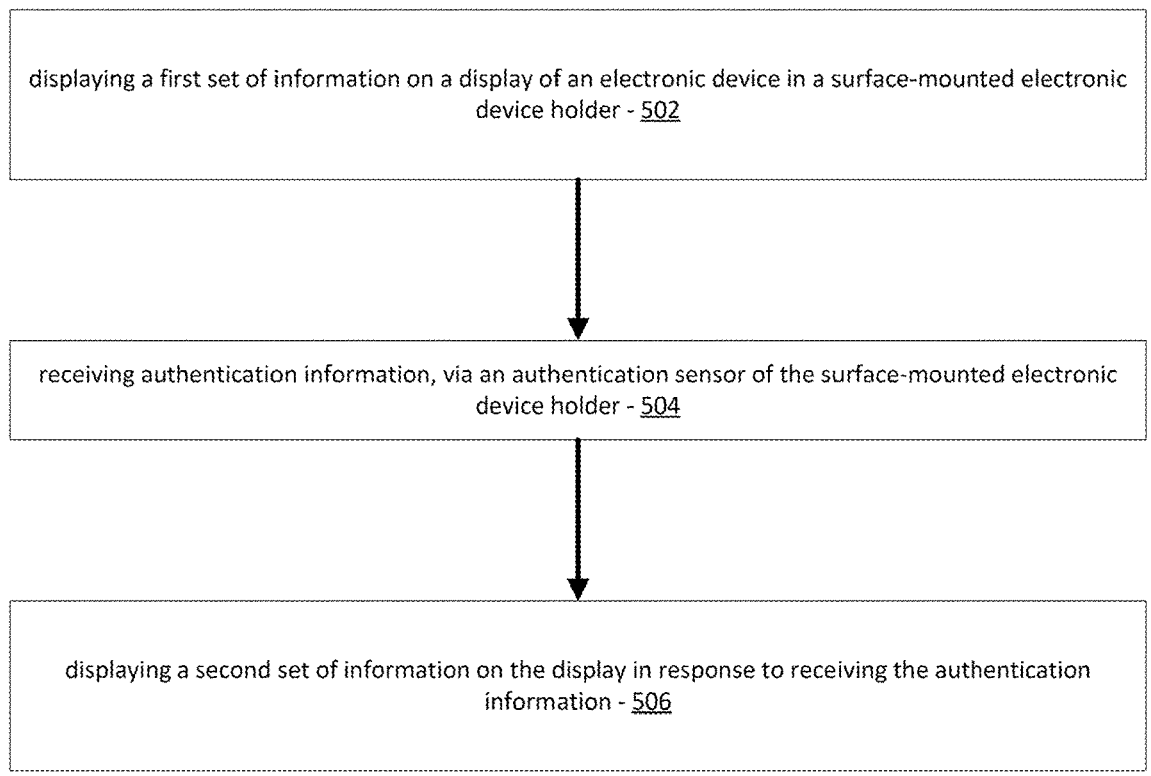
FIG. 23 is a simplified schematic diagram of a method of authenticating a user identity to display additional data at a wall-mounted electronic device within a PED holder assembly, in accordance with some embodiments.

FIG. 23 is a simplified schematic diagram of a method 500 of authenticating a user identity to display additional data at a wall-mounted electronic device within a PED holder assembly, in accordance with some embodiments.

At 502, the method 500 includes displaying a first set of information on a display of an electronic device in a surface-mounted electronic device holder. The first set of information may include generic information about a room or facility. The generic information may not include any personalized or secure information. The first information may be received from a remote device accessed over a wired connection to the electronic device. The electronic device in the surface-mounted electronic device holder may, for example, be positioned outside a patient room in a healthcare facility. Initially only information that is not privacy-protected may be displayed or visible on the screen. The information may be read-only such that no information may be editable or added prior to authentication.

At 504, the method 500 includes receiving authentication information, via an authentication sensor of the surface-mounted electronic device holder. The authentication sensor may include a proximity sensor, an RFID sensor, a biometric sensor, and other such devices to detect and verify an identify of an individual in proximity of the surface-mounted device holder. The electronic device may, for example receive a signal from a proximity sensor indicating an individual in proximity of the holder. In response, the electronic device may display a request for credentials or may activate one or more authentication devices for receiving authentication data. The electronic device may receive the credentials through the authentication device.

At 506, the method 500 includes displaying a second set of information on the display in response to receiving the authentication information. The second set of information may be displayed only after an identity of the individual is authenticated as in step 504. The second set of information may include healthcare data, such as a patient electronic health record or treatment records. Other such private information may be included in the second set of information. The second set of information may be read/write accessible such that an authenticated individual may add or revise information, for example to update a patient health or treatment log after visiting the patient. In some examples additional actions may be triggered by the electronic device after authenticating at 504. For example, a prompt may be displayed to wash or sanitize hands before entering the room, with a hand sanitizer connected to the electronic device capable of confirming use before allowing access into the room or before indicating, on the display, it is safe to proceed into the room. Additional data may be downloaded or uploaded to or from an individual's electronic device, such as a tablet of a treating physician to update a patient log in a hospital database following treatment of the patient.

Figure 24:
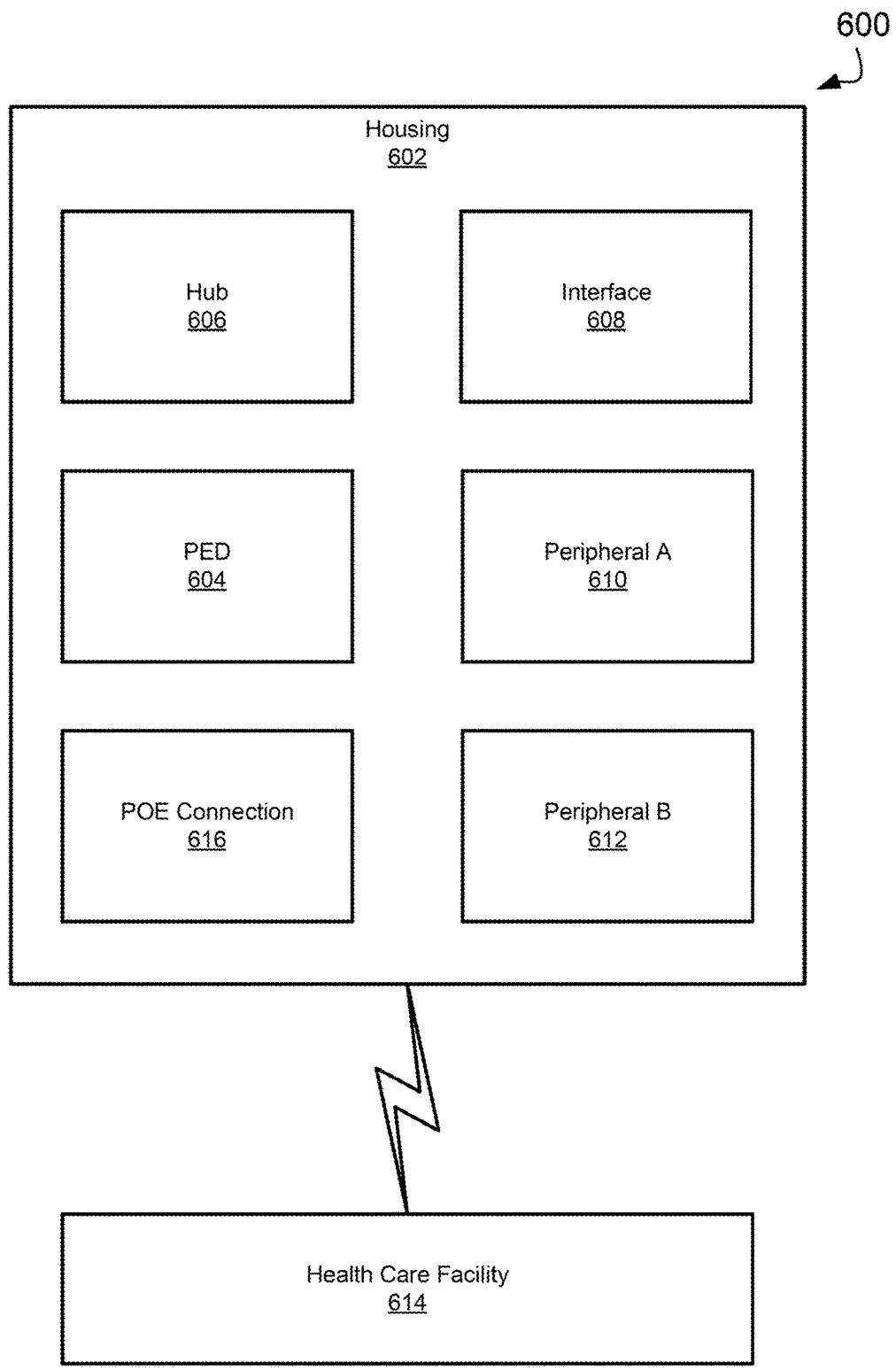
FIG. 24 is a simplified block diagram of elements included in a PED holder assembly and connections between system elements, in accordance with some embodiments.

FIG. 24 is a simplified block diagram of a system 600 of a PED holder assembly and connections between system elements, in accordance with some embodiments. The system includes a housing 602, a PED 604, a hub 606, an interface 608, a peripheral A 610, a peripheral B 612, a POE connection 616, and a health care facility system 614. The housing 602 may be the same as PED holder 14 or surface-mounted electronic device holder 304 described above, including any variations thereof. The housing 602 may connect to a surface of a health care facility, a rail of a bed in a health care facility, or any other rail or surface. The PED 604 is likewise similar to the PED described herein and may include a self-contained computing device and/or a custom-built computing device contained within the housing 602. The peripherals 610 and 612 may include additional devices such as lighting elements, projectors, authentication sensors, proximity sensors, communication devices, and other such additional components combined within the housing 602.

The housing 602 and the PED 604 may include or be connected to various systems and other elements as described herein, including the health care facility system 614, an interface 608, peripheral A 610, and peripheral B 612. The POE connection 616 may optionally provide power to the hub 606, the interface 608, the PED 604, and optionally to the peripherals 610 and 612 or other devices connected to the housing 602. The POE connection may provide data and power connections between the housing 602 and the health care facility 614. The elements within the housing 602 may be connected through wired connections, or may be connected through wireless, BLUETOOTH®, or any other communication means or technology. Additionally, the housing 602 may be able to perform all required calculations or logic and perform all methods internally, i.e., without connection to an external server. In some examples an external server, such as the health care facility system 614 may be in communication with the elements within the housing 602, over wired or wireless connections, such as POE connections as described herein, however the health care facility system 614 may not be performing the steps of the methods or any required actions. In some examples, the external server may perform some portion of the methods described herein.

The hub 606 may include connections to the various other elements within the housing 602 and may perform intermediate conveyance of instructions and data between different elements of the system. For example, the hub 606 may be connected to the PED 604 and the peripherals 610 and 612 through wired or wireless connections. The hub 606 may include a processor and memory and be capable of receiving instructions or data from the PED 604, the health care facility system 614, interface 608, or the peripherals 610 and 612 and communicating the data, or some portion of the data to any other system element. In an example, the PED 604 may send instructions to illuminate an illumination element, which may be peripheral A 610. The illumination element may include lights or projectors to illuminate an environment surrounding the housing 602 and may not, for example, include backlit elements for buttons or other such illumination devices. The hub 606 may receive the instructions from the PED 604 and may communicate with a driver of the illumination element to illuminate the lighting element in the instructed manner. In such examples, the hub may include wired connections to a driver board or circuit for the peripheral, or may include the driver elements for the peripherals as components of the hub 606.

In some examples, the interface 608 may include an assistance request button, such as the assistance request button 52 described above. The assistance request button may be actuated and cause a signal to be conveyed to the PED 604 through the hub 606. The hub may be capable of connecting to multiple devices such as the peripherals 610 and 612 in addition to the interface 608 while still only requiring a single connection to the PED 604, thereby enabling use of self-contained PED devices such as mobile devices and tablets.

The communications between the hub 606 and the PED 604 may be identified, i.e., to identify the source of a signal as from peripheral A 610 or interface 608 based on a pin identity associated with the hub 606. In some examples, data may be appended with an identity of a peripheral device associated with the data as it is manipulated and conveyed by the hub 606. In some examples, the PED 604 may act as a host device with the hub 606 acting as an agent of the PED 604.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A system comprising:
    a housing enclosing a space to contain an electronic device, the housing comprising a portion defining an opening through which a display of the electronic device is accessible by a user;
    one or more peripheral devices connected to the housing and controllable by the electronic device;
    a hub contained within the housing comprising:
        a first interface to couple the hub with the electronic device;
        a second interface for coupling to the one or more peripheral devices;
        a processor; and
        a non-transitory memory having instructions stored thereon that, when executed by the processor cause the processor to:
            receive first input data from the electronic device, the first input data indicating an instruction to be executed on one or more of the peripheral devices;
            send first output data from the hub to the one or more peripheral devices based on the instruction from the first input data;
            receive second input data from one or more of the one or more peripheral devices; and
            send second output data from the hub to the electronic device based on the second input data.

2. The system of claim 1, wherein the housing is adapted for mounting to a surface of a wall of a health care facility.

3. The system of claim 1, wherein the housing is adapted for mounting to a bed rail of a bed in a health care facility.

4. The system of claim 1, wherein the one or more peripheral devices comprise an assistance request button associated with requesting assistance in a health care facility, the assistance request button disposed in the housing.

5. The system of claim 4, wherein the second input data comprises input data from the assistance request button, and the second output data comprises an emergency request communicated to an emergency notification system of the health care facility via the electronic device.

6. The system of claim 1, wherein the one or more peripheral devices comprise an illumination element disposed around a perimeter of the housing.

7. The system of claim 6, wherein the illumination element comprises a projector configured to present image data on a surface of a health care facility.

8. The system of claim 6, wherein the first input data comprises instructions for illuminating the illumination element, and the first output data is conveyed to a driver of the illumination element.

9. The system of claim 1, further comprising a power over Ethernet (POE) connection within the housing, the POE connection providing a power connection to the hub and a power and data connection to the electronic device.

10. The system of claim 9, wherein the POE connection further provides a data connection to the hub.

* * * * *